US012140525B2

United States Patent
Takatsuka et al.

(10) Patent No.: US 12,140,525 B2
(45) Date of Patent: Nov. 12, 2024

(54) MEASURING DEVICE AND IMAGING CONTROL METHOD

(71) Applicant: Sony Group Corporation, Tokyo (JP)

(72) Inventors: Susumu Takatsuka, Tokyo (JP); Hiroki Tetsukawa, Tokyo (JP)

(73) Assignee: SONY GROUP CORPORATION, Tokyo (JP)

(*) Notice: Subject to any disclaimer, the term of this patent is extended or adjusted under 35 U.S.C. 154(b) by 100 days.

(21) Appl. No.: 17/911,423

(22) PCT Filed: Mar. 22, 2021

(86) PCT No.: PCT/JP2021/011766
§ 371 (c)(1),
(2) Date: Sep. 14, 2022

(87) PCT Pub. No.: WO2021/215173
PCT Pub. Date: Oct. 28, 2021

(65) Prior Publication Data
US 2023/0102792 A1    Mar. 30, 2023

(30) Foreign Application Priority Data

Apr. 22, 2020   (JP) ................................ 2020-075926
Sep. 25, 2020   (JP) ................................ 2020-160639

(51) Int. Cl.
*G06V 10/25*   (2022.01)
*G01N 15/14*   (2006.01)
(Continued)

(52) U.S. Cl.
CPC ....... *G01N 15/1433* (2024.01); *G01N 15/147* (2013.01); *G06T 7/74* (2017.01);
(Continued)

(58) Field of Classification Search
None
See application file for complete search history.

(56) References Cited

U.S. PATENT DOCUMENTS

| | | | |
|---|---|---|---|
| 2010/0053614 A1* | 3/2010 | Jeys | G01N 15/1434 356/337 |
| 2017/0082530 A1* | 3/2017 | Sieracki | G01N 15/1433 |
| 2017/0116748 A1 | 4/2017 | Scutaru et al. | |

FOREIGN PATENT DOCUMENTS

| | | |
|---|---|---|
| JP | 6-194299 A | 7/1994 |
| JP | 2016-95259 A | 5/2016 |
| WO | 2020/080139 A1 | 4/2020 |

OTHER PUBLICATIONS

International Search Report and Written Opinion mailed on Jun. 8, 2021, received for PCT Application PCT/JP2021/011766, filed on Mar. 22, 2021, 13 pages including English Translation.
(Continued)

*Primary Examiner* — Samuel D Fereja
(74) *Attorney, Agent, or Firm* — XSENSUS LLP

(57) ABSTRACT

A measuring device according to the present technology includes a light emitting unit configured to emit light to a fluid, a light receiving unit configured to perform photoelectric conversion for incident light using an electron avalanche phenomenon by a plurality of pixels to obtain a light reception signal, and a control unit configured to perform processing of detecting a target object in the fluid on the basis of the light reception signal and execute an imaging operation of the target object on condition that the target object is detected.

20 Claims, 30 Drawing Sheets

(51) Int. Cl.
  *G01N 15/1433* (2024.01)
  *G06T 7/73* (2017.01)
  *G06V 10/60* (2022.01)
  *G06V 10/75* (2022.01)
  *G06V 20/69* (2022.01)
  *H04N 23/56* (2023.01)
  *H04N 23/60* (2023.01)
  *G01N 15/00* (2006.01)
  *G01N 15/01* (2024.01)

(52) U.S. Cl.
  CPC .............. *G06V 10/25* (2022.01); *G06V 10/60* (2022.01); *G06V 10/751* (2022.01); *G06V 20/698* (2022.01); *H04N 23/56* (2023.01); *H04N 23/60* (2023.01); *G01N 2015/0053* (2013.01); *G01N 15/01* (2024.01); *G06V 2201/07* (2022.01)

(56) References Cited

OTHER PUBLICATIONS

Rocca et al., "Real-Time Fluorescence Lifetime Actuation for Cell Sorting using a CMOS SPAD Silicon Photomultiplier", Optics Letters, vol. 41, No. 4, Dec. 26, 2015, pp. 673-676.
Mai et al., "Flow cytometry visualization and real-time processing with a CMOS SPAD array and high-speed hardware implementation algorithm", Proc.of SPIE, vol. 11243, 112430S, Feb. 17, 2020, pp. 112430S-1-112430S-7.

* cited by examiner

| TARGET PARTICLE-1 ||
|---|---|
| CLASS PARTICLE NAME | Plankton A |
| SIZE | 20um TO 40um |
| WAVELENGTH COMPONENT | 650±10nm |
| IMAGE DATA (REPRESENTATIVE IMAGE OBTAINED FROM Plankton A LEARNING DATA) |  |

| TARGET PARTICLE-2 ||
|---|---|
| CLASS PARTICLE NAME | null |
| SIZE | 20um TO 40um |
| WAVELENGTH COMPONENT | 650±20nm |
| IMAGE DATA | null |

550nm filter

B

600nm filter

C

650nm filter

D

700nm filter

20um TO 40um

MATCH CONDITION OF TARGET PARTICLE

*FIG. 14*

550nm filter

600nm filter

⇩ MATCH CONDITION OF TARGET PARTICLE

650nm filter

700nm filter 1E (MEASURING DEVICE)

MEASURING DEVICE AND IMAGING CONTROL METHOD

CROSS-REFERENCE TO RELATED APPLICATIONS

The present application is based on PCT filing PCT/JP2021/011766, filed Mar. 22, 2021, which claims priorities to Japanese Patent Application Nos. 2020-075926, filed Apr. 22, 2020 and 2020-160639, filed Sep. 25, 2020, the entire contents of each are incorporated herein by reference.

TECHNICAL FIELD

The present technology relates to a technical field of a measuring device and an imaging control method of the measuring device for measuring a target object included in a fluid, such as plankton contained in water, for example, on the basis of a captured image.

BACKGROUND ART

Conventionally, in microorganism measurement in water, a method of inspecting a sample on land, the sample having been collected by a water collector for each water depth, been adopted. Therefore, it takes time and effort and lacks immediacy.

Therefore, for example, as in the following Patent Document 1, there is a technology for solving the problem by mounting a microorganism measuring device equipped with an automatic identification function on an autonomous underwater vehicle (AUV) or an underwater drone.

However, in the method of Patent Document 1, after a sample is passed through a flow cell, imaging and identification are performed regardless of the presence or absence of microorganisms in the sample. Therefore, there is a problem that large power consumption is required for imaging.

Since the space of an exploratory vessel and the capacity of a battery to be mounted are limited, the measuring device is required to be as small as possible and to operate in a power-saving manner.

Patent Document 2 below discloses that the presence or absence of microorganisms in a sample is detected by detecting weak light excited by the microorganisms when predetermined light such as laser light is emitted, and the sample is imaged at timing triggered by detection of the microorganisms. According to the method of Patent Document 2, it is not necessary to constantly perform imaging for measurement regardless of the presence or absence of microorganisms in a sample, and it is possible to achieve power saving.

CITATION LIST

Patent Document

Patent Document 1: Japanese Patent Application Laid-Open No. 2016-95259
Patent Document 2: US 2017-82530 A

SUMMARY OF THE INVENTION

Problems to be Solved by the Invention

However, in the method of Patent Document 2, a single (single-pixel) photomultiplier tube is used as a light receiving sensor for detecting the presence or absence of microorganisms, and imaging is performed in response to detection of return light from the microorganisms in a single pixel. Specifically, imaging is performed in response to detection of return light of a specific wavelength in the single pixel. Since the start condition of the imaging is simply detection of the return light of a specific wavelength, there is a high possibility that the return light reacts to something other than the microorganisms, and there is a difficulty in detection accuracy of the presence or absence of the microorganisms. When the detection accuracy of the presence or absence of microorganisms is low, imaging may be performed even in a case where no microorganisms are present in the sample, and it is difficult to achieve power saving.

The present technology has been made in view of the above circumstances, and an object of the present technology is to achieve power saving in a measuring device that measures a target object in a fluid, such as a measuring device for microorganisms in water, for example.

Solutions to Problems

A first measuring device according to the present technology includes: a light emitting unit configured to emit light to a fluid; a light receiving unit configured to perform photoelectric conversion for incident light using an electron avalanche phenomenon by a plurality of pixels to obtain a light reception signal; and a control unit configured to perform processing of detecting a target object in the fluid on the basis of the light reception signal and execute an imaging operation of the target object on condition that the target object is detected.

According to the above configuration, it is possible to detect the presence or absence of the target object on the basis of the light reception signals of the plurality of pixels in reducing power consumption related to imaging by performing the imaging of the target object triggered by the detection of the target object on the basis of the light reception signal of the light receiving unit instead of constantly performing the imaging of the target object.

In the above-described first measuring device according to the present technology, it is conceivable that the light receiving unit includes a SPAD element as a photoelectric conversion element.

Thereby, it is not necessary to use a large-sized and high-power-consumption photoelectric conversion element such as a photomultiplier tube as the light receiving unit.

In the above-described first measuring device according to the present technology, it is conceivable that the control unit performs the processing of detecting the target object on the basis of an image feature of a light receiving reaction portion in the light receiving unit.

The "image feature of the light receiving reaction portion" referred to here means a feature of an image including at least one or more pixels having a light receiving reaction as the light receiving reaction portion, such as an image size or a position of the light receiving reaction portion, a wavelength of received light, or a value of the light reception signal.

In the above-described first measuring device according to the present technology, it is conceivable that the control unit prevents imaging of an imaging range corresponding to the light receiving reaction portion in a case where the image feature of the light receiving reaction portion does not match a designated image feature.

Thereby, it is possible to prevent an object other than an object having the designated image feature from being recklessly imaged.

In the first measuring device according to the present technology described above, it is conceivable that the control unit detects, as the image feature, a pixel position and an image size of the light receiving reaction portion.

Thereby, it is possible to specify a pixel range in which the target object is captured, that is, a pixel range in which imaging is to be performed, for an imaging sensor that images the target object.

In the above-described first measuring device according to the present technology, it is conceivable that the control unit performs control such that, in an imaging sensor that images the target object, the imaging operation is performed only for a partial pixel range in which the target object is captured.

Thereby, the power consumption related to imaging can be reduced as compared with a case where the imaging operation is performed for the entire pixel range in the imaging sensor.

In the above-described first measuring device according to the present technology, it is conceivable that the control unit performs matching between a captured image and a template image for the partial pixel range.

By performing the matching based on the captured image, it is possible to appropriately identify the type of the target object.

In the above-described first measuring device according to the present technology, it is conceivable that the control unit performs class identification of an object captured in the captured image for the partial pixel range, and performs the matching using the template image of an identified class among the template images prepared for each class.

By performing the image matching after narrowing the class in this manner, it is possible to improve the efficiency of image matching processing.

In the above-described first measuring device according to the present technology, it is conceivable that the control unit sets a bounding box as a range surrounding the target object from the captured image of the partial pixel range and sets an ROI that is a region including the bounding box and larger in size than the bounding box in a reference frame that is a predetermined frame when or after the target object is detected on the basis of the light reception signal, and sets the bounding box of the target object and sets the ROI based on the bounding box in the ROI set in a previous frame, in a frame after the reference frame.

Thereby, it is possible to track the target object even in a case where the target object moves in the captured image.

In the above-described first measuring device according to the present technology, it is conceivable that a sensor that functions as the light receiving unit and an imaging sensor that images the target object on the basis of control of the control unit are separated.

Thereby, existing sensors can be used as a sensor that functions as the light receiving unit (a sensor that performs the photoelectric conversion using an electron avalanche phenomenon) and an imaging sensor that images a target object.

The above-described first measuring device according to the present technology is conceivable to include a single sensor having a function as the light receiving unit and a function to image the target object on the basis of control of the control unit.

In the case of separately providing the sensors, it is necessary to provide a spectroscopic means for distributing light from the fluid to each of the sensors. However, the integrated sensor eliminates the need to provide such a spectroscopic means.

The above-described first measuring device according to the present technology is conceivable to include a flow cell in which the fluid is sampled with respect to an internal flow path, in which the control unit causes a fluid different from the fluid as a sample to flow into the flow path to clean the flow cell after completion of the imaging operation.

Thereby, it is possible to prevent occurrence of erroneous measurement such as re-measurement of a measured target object.

In the above-described first measuring device according to the present technology, it is conceivable that the control unit performs the processing of detecting the target object on the basis of the light reception signal after the different fluid flows into the flow path.

Thereby, it is possible to confirm the presence or absence of a target object remaining after cleaning.

An imaging control method according to the present technology is an imaging control method of a measuring device including at least a light emitting unit configured to emit light to a fluid and a light receiving unit configured to perform photoelectric conversion for incident light using an electron avalanche phenomenon by a plurality of pixels to obtain a light reception signal, the imaging control method including: performing processing of detecting a target object in the fluid on the basis of the light reception signal and executing an imaging operation of the target object on condition that the target object is detected.

According to such an imaging control method, effects similar to the effects of the above-described first measuring device according to the present technology can be obtained.

A second measuring device according to the present technology includes: a light emitting unit configured to emit light to a fluid; an imaging sensor configured to perform photoelectric conversion for incident light by a plurality of pixels to obtain a light reception signal; and a control unit configured to perform processing of detecting a target object in the fluid on the basis of the light reception signal, and cause the imaging sensor to execute an imaging operation of the target object on condition that the target object is detected, in which the control unit performs control such that the imaging operation is performed only for a partial pixel range in which the target object is captured as the imaging operation of the target object.

According to the above configuration, it is possible to reduce the power consumption related to imaging by performing the imaging of the target object triggered by the detection of the target object on the basis of the light reception signal instead of constantly imaging the target object. Furthermore, the power consumption related to imaging can be reduced as compared with a case where the imaging operation is performed for the entire pixel range in the imaging sensor.

Furthermore, in the above-described second measuring device according to the present technology, it is possible that the control unit performs matching between a captured image and a template image for the partial pixel range.

By performing the matching based on the captured image, it is possible to appropriately identify the type of the target object.

Moreover, in the above-described second measuring device according to the present technology, it is possible that the control unit performs class identification of an object captured in the captured image for the partial pixel range, and performs the matching using the template image of an identified class among the template images prepared for each class.

By performing the image matching after narrowing the class in this manner, it is possible to improve the efficiency of image matching processing.

BRIEF DESCRIPTION OF DRAWINGS

FIG. 11 is explanatory diagrams of an example of a case where the SPAD sensor is provided for each wavelength.

FIG. 14 is explanatory diagrams of an example of detection processing in a case of using the sensor of FIG. 11.

MODE FOR CARRYING OUT THE INVENTION

Hereinafter, an embodiment will be described in the following order.

<1. Configuration of Measuring device>
<2. Measuring Method as Embodiment>
<3. Processing Procedure>
<4. Sensor Structure>
<5. Imaging Sensor>
<6. Modification>
 [6-1. First Modification]
 [6-2. Second Modification]
 [6-3. Third Modification]
 [6-4. Fourth Modification]
 [6-5. Fifth Modification]
 [6-6. Sixth Modification]
<7. Summary of Embodiment>
<8. Present Technology>

1. Configuration of Measuring Device

First, a configuration of a measuring device 1 as an embodiment according to the present technology will be described.

The measuring device 1 is a device that measures a target object contained in a fluid taken in as a sample, such as microorganisms contained in seawater, for example. Specifically, the measuring device 1 of the present example takes in seawater, lake water, or the like as the sample, and measures the target object such as plankton contained in the sample. The measurement here is a concept including at least any of identification of the number, type, or feature of the target objects, or recording or storage of a captured image of the target object.

Figure 1:
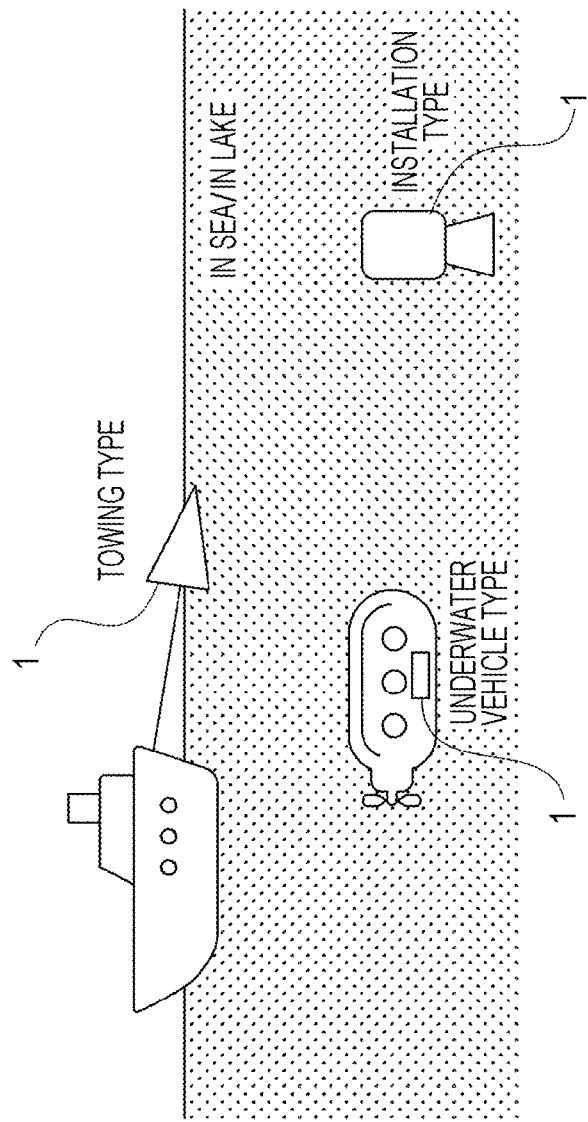
FIG. 1 is a diagram for describing an example of a device form of a measuring device as an embodiment.

FIG. 1 is a diagram for describing an example of a device form of the measuring device 1.

As illustrated in the drawing, as the measuring device 1, for example, a towing type towed by a vessel that navigates on the sea or on the lake or an installation type installed in the sea or in the lake can be adopted. Alternatively, a device form as an underwater vehicle type installed in an underwater vehicle that navigates in the sea or lake can be adopted.

Figure 2:
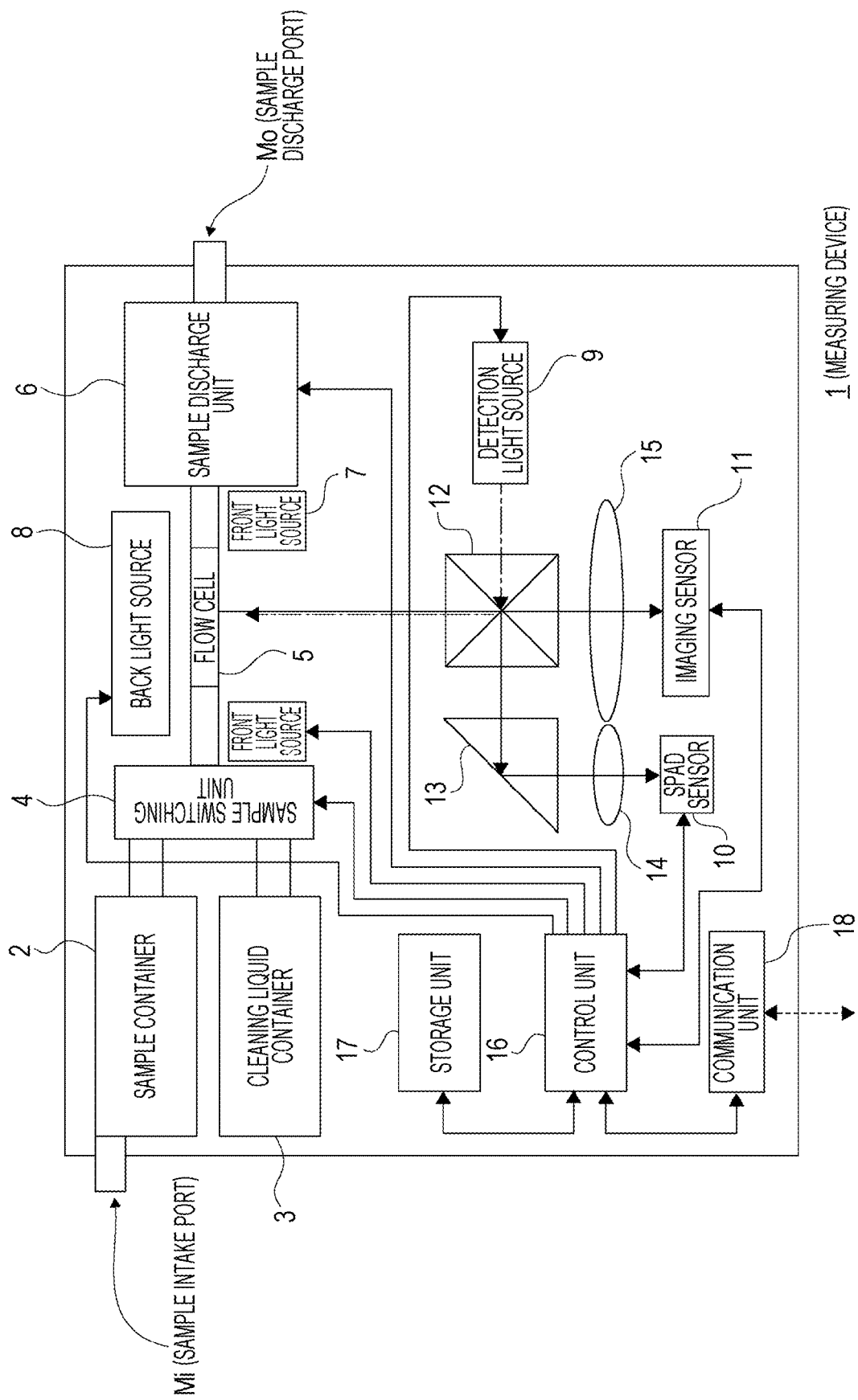
FIG. 2 is a block diagram illustrating an internal configuration example of the measuring device as the embodiment.

FIG. 2 is a block diagram illustrating an internal configuration example of the measuring device 1.

As illustrated, the measuring device 1 includes a sample container 2, a cleaning liquid container 3, a sample switching unit 4, a flow cell 5, a sample discharge unit 6, a front light source 7, a back light source 8, a detection light source 9, a single photon avalanche diode (SPAD) sensor 10, an imaging sensor 11, a half mirror 12, a mirror 13, a lens 14, a lens 15, a control unit 16, a storage unit 17, and a communication unit 18.

The sample container 2 is a container that stores the fluid (seawater or lake water in the present example) as the sample, and stores the sample taken in from outside of the device through a sample intake port Mi.

The cleaning liquid container 3 is a container that stores a cleaning liquid for cleaning a flow path in the flow cell 5.

The sample switching unit 4 switches the fluid to flow into the flow path in the flow cell 5 between the sample from the sample container 2 and the cleaning liquid from the cleaning liquid container 3.

The flow cell 5 functions as a sample storage unit, and the fluid as the sample is sampled with respect to the flow path formed inside. Note that, as will be described below, in a state where the sample switching unit 4 is switched to the cleaning liquid container 3 side, the cleaning liquid flows into the flow path of the flow cell 5.

The sample discharge unit 6 has a pump for fluid discharge, and discharges the fluid in the flow path of the flow cell 5 through a sample discharge port Mo located outside the device when the pump is driven.

Here, in the present example, the flow path from the sample container 2 to the sample discharge unit 6 via the sample switching unit 4→the flow cell 5 and the flow path from the cleaning liquid container 3 to the sample discharge unit 6 via the sample switching unit 4→the flow cell 5 are consistent, and the inflow of the sample from the sample container 2 to the flow cell 5 and the inflow of the cleaning liquid from the cleaning liquid container 3 to the flow cell 5 are performed by driving the pump of the sample discharge unit 6.

The front light source 7 is a light source for illuminating the fluid in the flow cell 5 at the time of imaging by the imaging sensor 11. Here, the "front" means a surface on the imaging sensor 11 side with respect to the position of the flow cell 5. In the present example, the front light source 7 is an annular light source, and prevents interference with imaging by the imaging sensor 11, and obliquely illuminates the sample from the front side of the flow cell 5.

Similarly to the front light source 7, the back light source 8 is a light source for illuminating the fluid in the flow cell 5 at the time of imaging by the imaging sensor 11, and is located on the opposite side of the front light source 7 with respect to the flow cell 5.

Here, roles of the front light source 7 and the back light source 8 will be described.

Figure 3:
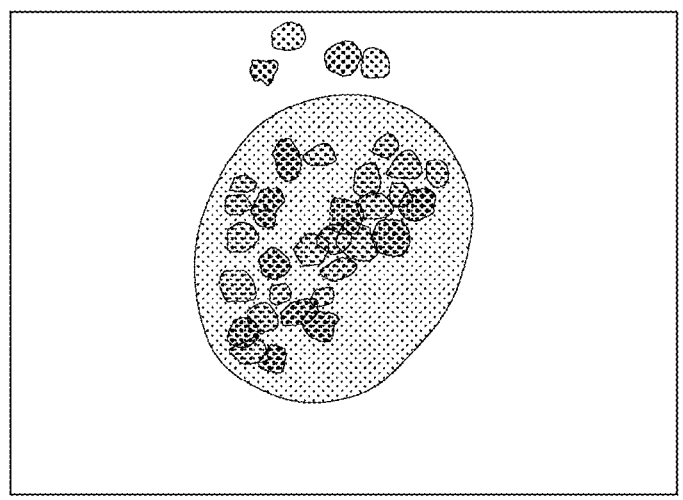
FIG. 3 is a view illustrating an example of a captured image at the time of illumination by a back light source.
Figure 4:
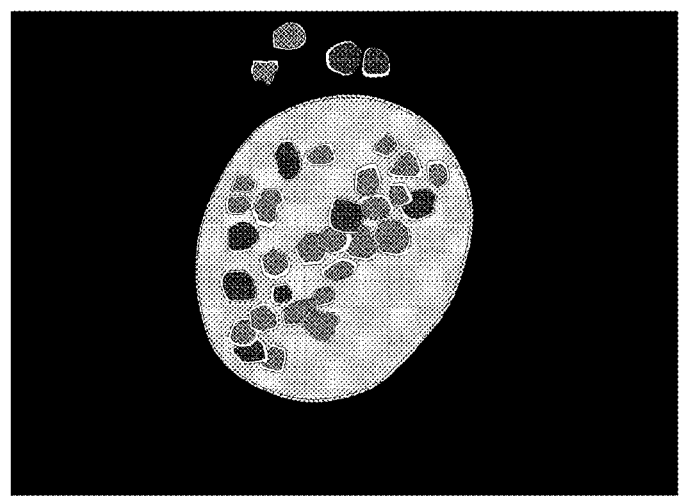
FIG. 4 is a view illustrating an example of a captured image at the time of illumination by a front light source.

FIG. 3 illustrates an example of a captured image at the time of illumination by the back light source 8, and FIG. 4 illustrates an example of a captured image at the time of illumination by the front light source 7.

The back light source 8 is used for bright field of view imaging. The imaging sensor 11 receives light transmitted through the sample, which is similar to a method used in a general microscope. Since illumination light directly enters the lens 15, background becomes bright.

Meanwhile, the front light source 7 is used for dark field of view imaging. Light is applied from an oblique side of the sample, and scattered light and reflected light of the target object are received by the imaging sensor 11. Even a transparent object can be measured finely with high contrast. In this case, since the illumination light does not directly enter the lens 15, the background becomes dark.

In FIG. 2, the detection light source 9 emits light for detecting the target object to the sample sampled in the flow cell 5. As the detection light source 9, for example, a semiconductor laser or the like is used. As illustrated in the drawing, the light emitted from the detection light source 9 is reflected by the half mirror 12 and applied to the fluid sampled in the flow path in the flow cell 5.

The SPAD sensor 10 functions as a sensor for detecting the target object in the fluid in the flow cell 5. In the measuring device 1 of the embodiment, a pixel array in which a plurality of photodetection pixels is arranged is used to detect weak light of microorganisms or particles. The SPAD is considered as one of the techniques of the photodetection pixel. In the SPAD, avalanche amplification occurs when one photon enters a PN junction region of a high electric field in a state where a voltage larger than a breakdown voltage is applied. At this time, by detecting the position and timing of a pixel through which a current instantaneously flows, the presence or absence, position, size, and the like of microorganisms or particles in the flow cell 5 can be specified.

The SPAD sensor 10 includes a SPAD element that performs photoelectric conversion for incident light, using an electron avalanche phenomenon. The electron avalanche phenomenon in the SPAD element is a kind of phenomenon known as an internal photoelectric effect. The internal photoelectric effect is a phenomenon in which conduction electrons in a substance increase when a semiconductor or an insulator is irradiated with light.

As is known, the SPAD element is an element having a light receiving resolution in units of photons. In other words, the element is capable of identifying the presence or absence of light reception in units of photons.

The SPAD sensor 10 in the present example has a configuration in which a plurality of pixels having the SPAD elements is two-dimensionally arrayed.

The light emitted from the target object in the fluid in the flow cell 5 enters the SPAD sensor 10 via the half mirror 12, the mirror 13, and the lens 14.

The imaging sensor 11 is configured as an image sensor of a charge coupled device (CCD) type, a complementary metal oxide semiconductor (CMOS) type, or the like, for example, and a plurality of pixels having photoelectric conversion elements is two-dimensionally arrayed. The photoelectric conversion element included in each pixel of the imaging sensor 11 does not perform photoelectric conversion using an electron avalanche phenomenon, and for example, a photoelectric conversion element used in general imaging such as a photodiode is adopted. That is, the photoelectric conversion element is a photoelectric conversion element having a lower light receiving resolution than the SPAD element.

The imaging sensor 11 performs imaging for the flow path in the flow cell 5 (imaging including at least the flow path in an imaging field of view). Light (image light) from the flow cell 5 passes through the half mirror 12 and enters the imaging sensor 11 via the lens 15.

The control unit 16 includes, for example, a microcomputer including a central processing unit (CPU), a read only memory (ROM), and a random access memory (RAM), and performs overall control of the measuring device 1. For example, the control unit 16 performs switching control of the sample switching unit 4, light emission drive control of the front light source 7 and the back light source 8, drive control of the pump in the sample discharge unit 6, light emission drive control of the detection light source 9, and the like.

Furthermore, the control unit 16 performs processing of reading data stored in the storage unit 17, processing of storing data in the storage unit 17, and exchange of various data with an external device via the communication unit 18. For example, the storage unit 17 includes a nonvolatile memory. The communication unit 18 performs data communication with an external device by wired or wireless means.

Furthermore, the control unit 16 of the present example performs object detection processing based on the light reception signal by the SPAD sensor 10, various types of image analysis processing based on the captured image by the imaging sensor 11, and the like, and these pieces of processing will be described again below.

2. Measuring Method as Embodiment

A measuring method as the embodiment will be described.

Figure 5:
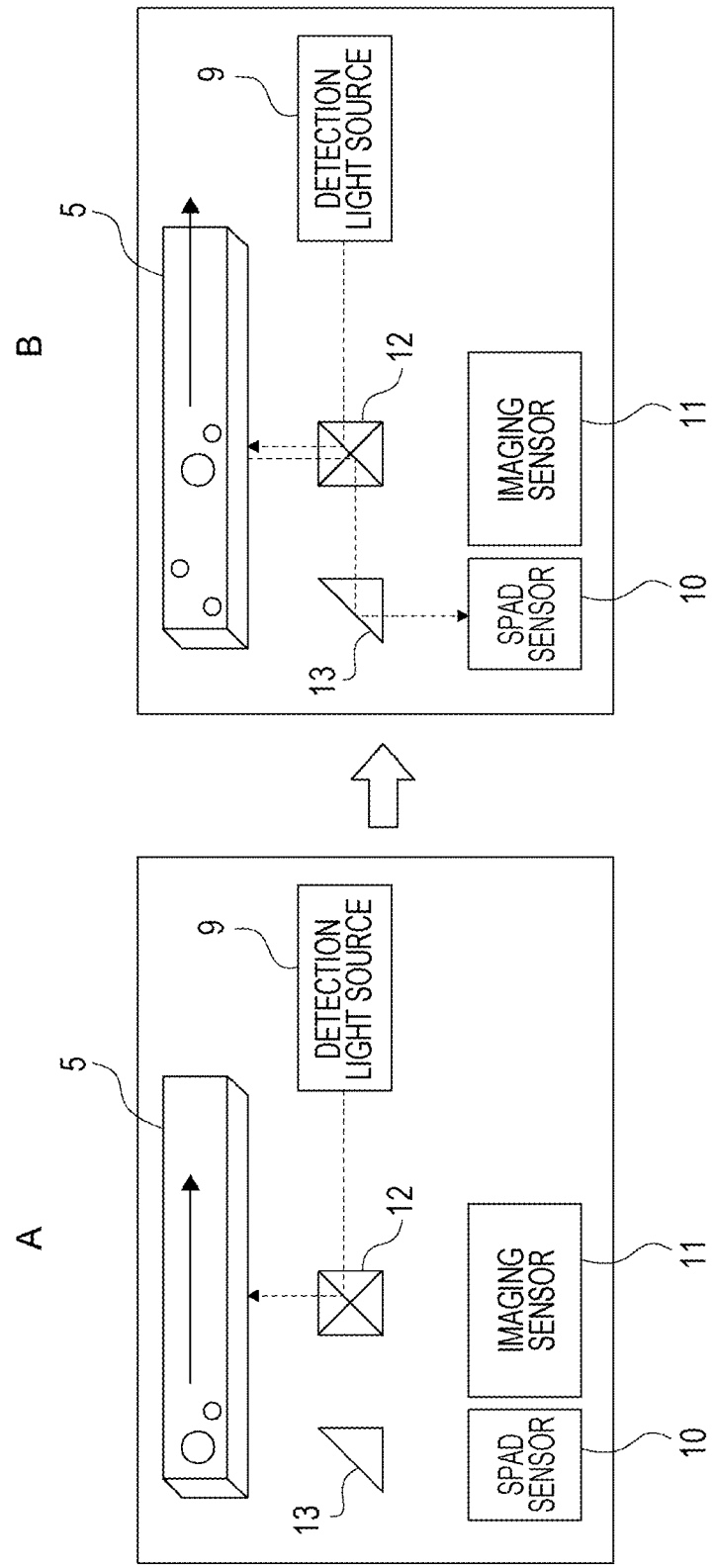
FIG. 5 is an explanatory diagram of processing of detecting a target object as the embodiment.

FIG. 5 is an explanatory diagram of processing of detecting the target object in the sample.

First, as illustrated in FIG. 5A, in the state where the fluid as the sample is sampled in the flow cell 5, the detection light source 9 is caused to emit light to irradiate the sample with detection light.

Here, at the time of measurement, the fluid as the sample is moved in a discharge direction (the direction of the sample discharge port Mo) in the flow path of the flow cell 5. That is, the pump of the sample discharge unit 6 is driven, and the fluid is gradually moved in the discharge direction.

As illustrated in FIG. 5A, in a state where the target object in the sample does not appear in the field of view, the SPAD sensor 10 does not receive the return light from the target object.

On the other hand, when the target object appears in the field of view as illustrated in FIG. 5B, the return light from the target object based on the light emitted from the detection light source 9 is received by the SPAD sensor 10.

Here, in a case where the target object is phytoplankton, the return light becomes light excited by the phytoplankton by a fluorescence reaction based on the irradiation light of the detection light source 9. Furthermore, in a case where the target object is zooplankton, the return light is scattered light generated in the zooplankton on the basis of the irradiation light of the detection light source 9.

In the measuring method of the present embodiment, in a case where the return light from the sample side is received by the SPAD sensor 10 as a result of irradiating the sample with the detection light as described, an imaging operation by the imaging sensor 11 is performed. That is, in a case where the return light is not received, the imaging operation by the imaging sensor 11 is not performed, so that power consumption related to imaging is reduced.

At this time, by using the SPAD sensor 10 as the light receiving unit of the return light, it is possible to reduce the size and power consumption of the light receiving unit as compared with the case of adopting a conventional light receiving unit using a photomultiplier tube.

Here, to appropriately determine the presence or absence of reception of the return light from the target object, an influence of noise caused by a dark current should be considered.

To appropriately eliminate such an influence of noise, in the present example, the following method is adopted for object detection method based on the light reception signal of the SPAD sensor 10.

Figure 6:
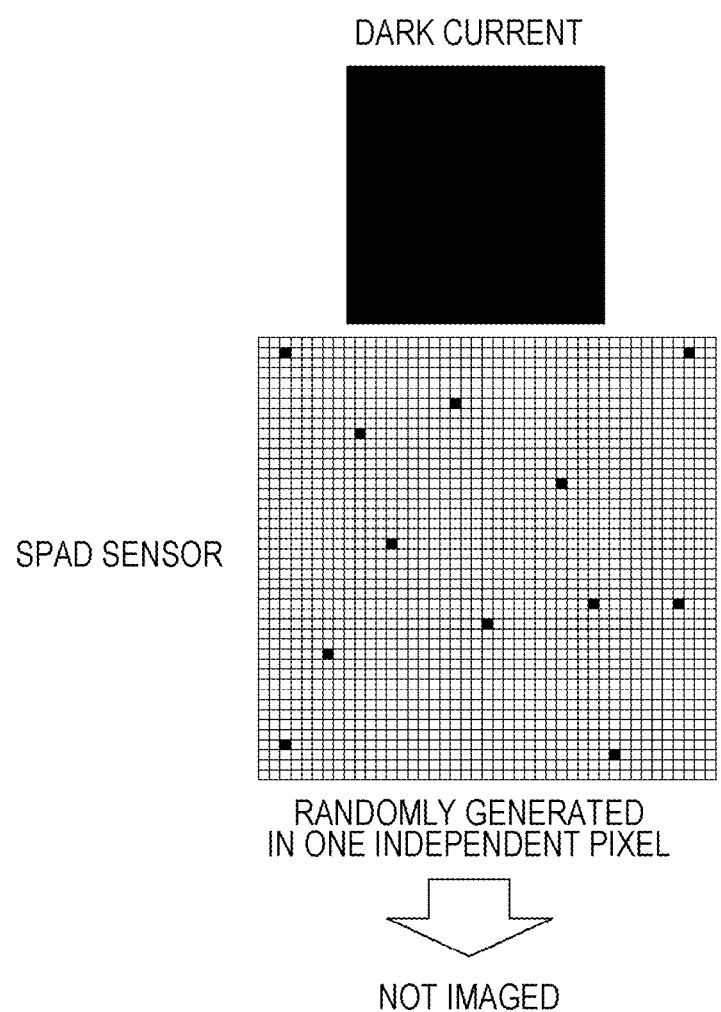
FIG. 6 is a view illustrating an example of noise caused by a dark current.

FIG. 6 illustrates an example of noise caused by a dark current.

As illustrated, the noise is randomly generated in one independent pixel.

Figure 7:
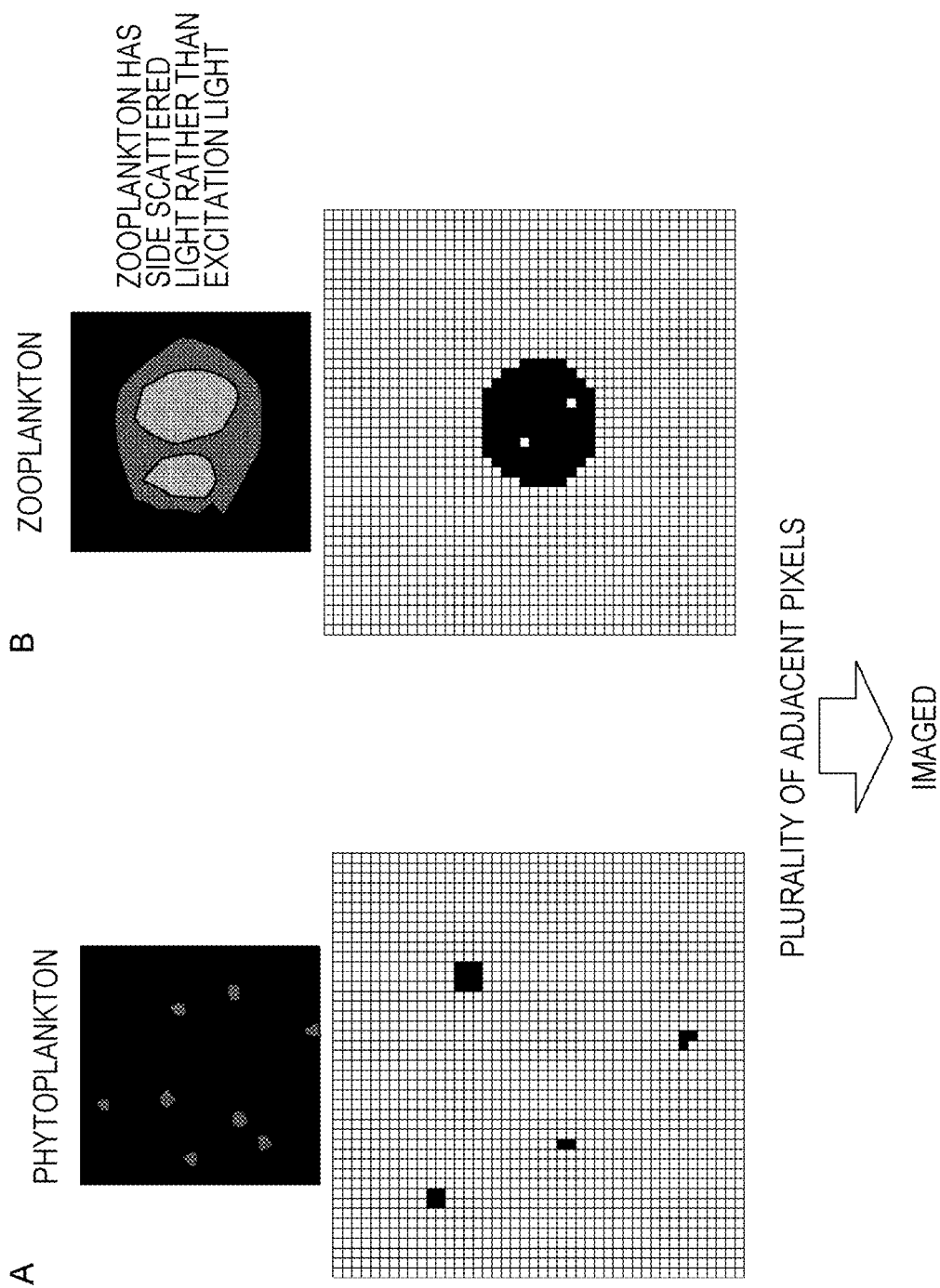
FIG. 7 is a view of countermeasures against noise in the processing of detecting a target object.

Therefore, in the present example, as illustrated in FIG. 7, a method of determining a region of a plurality of adjacent pixels as a light receiving region of the return light from the target object in a case where light reception is recognized in the region is adopted.

FIG. 7A illustrates an example of the light receiving region (the black pixels in the drawing) of the return light from phytoplankton, and FIG. 7B illustrates an example of the light receiving region of the return light from zooplankton.

In the case where the reception of the return light from the target object is recognized as illustrated in these drawings, imaging using the imaging sensor 11 is performed.

Note that, in eliminating the influence of noise, it is also possible to take countermeasures against noise by causing the detection light source 9 to emit pulse light (blink light) and synchronizing the light reception timing of the SPAD sensor 10 with the pulse light.

Here, information (hereinafter referred to as "definition information I1") defining a target object to be measured is set in advance for the measuring device 1.

Figures 8, 9:
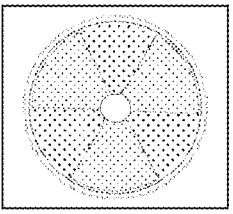
FIG. 8 is a diagram illustrating an example of definition information.
FIG. 9 is a diagram illustrating another example of definition information.

FIGS. 8 and 9 illustrate examples of the definition information I1.

For example, as illustrated in FIG. 8, the definition information I1 can be information including class particle name, size, wavelength component, and image data of the target object. As the class particle name, for example, information of a specific name is determined in the case where the target object is plankton. The size information is information indicating size classification of the target object, and is, for example, information having a range such as "20 to 40 μm" illustrated in the drawing. Furthermore, the wavelength component information is information defining a wavelength component of the return light corresponding to the irradiation light of the detection light source 9. The image data is image data (image data) of the target object. As the image data, data actually captured for one individual of the target object can be used, or representative image data obtained by machine learning from captured images of a plurality of individuals can be used.

Furthermore, the definition information I1 may be information designating only some features as illustrated in FIG. 9, other than the information designating the specific target object as illustrated in FIG. 8.

FIG. 9 illustrates an example of the definition information I1 designating only the size and the wavelength component of the target object to be measured.

In the measuring device 1, these pieces of definition information I1 are stored in, for example, the storage unit 17 illustrated in FIG. 2.

To detect the presence or absence of the target object in the sample according to the definition information I1 as illustrated in FIGS. 8 and 9, the SPAD sensor 10 is required to be able to identify the wavelength of the received light.

A configuration of the SPAD sensor 10 for implementing such a wavelength identification function will be described with reference to FIGS. 10 and 11.

Figure 10:
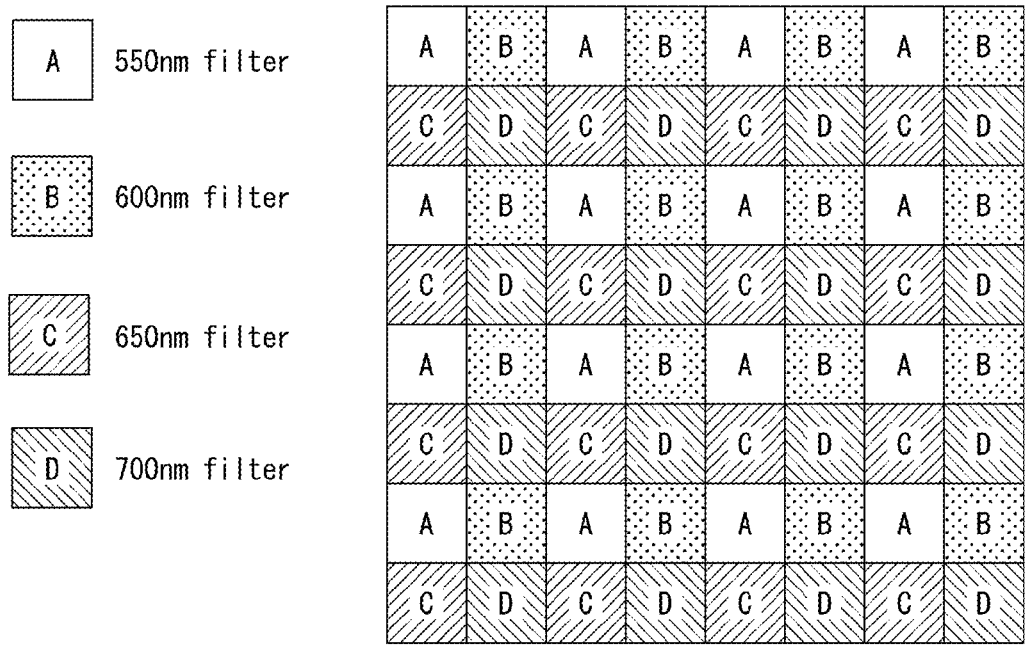
FIG. 10 is a diagram illustrating an example of an SPAD sensor provided with a different wavelength filter for each pixel.

FIG. 10 is an example in which a different wavelength filter is provided for each pixel of the SPAD sensor 10.

In the drawing, a pixel denoted by "A" is a pixel provided with a wavelength filter having a wavelength of 550 nm (hereinafter referred to as "pixel A"), a pixel denoted by "B" is a pixel provided with a wavelength filter having a wavelength of 600 nm (hereinafter referred to as "pixel B"), a pixel denoted by "C" is a pixel provided with a wavelength filter having a wavelength of 650 nm (hereinafter referred to as "pixel C"), and a pixel denoted by "D" is a pixel provided with a wavelength filter having a wavelength of 700 nm (hereinafter referred to as "pixel D"). In the SPAD sensor 10 in this case, the A pixel, the B pixel, the C pixel, and the D pixel are arranged so as to be present every other pixel in each of a horizontal direction (row direction) and a vertical direction (column direction).

With such a configuration, it is possible to specify at which pixel position the light with any wavelength is received.

Figure 11:
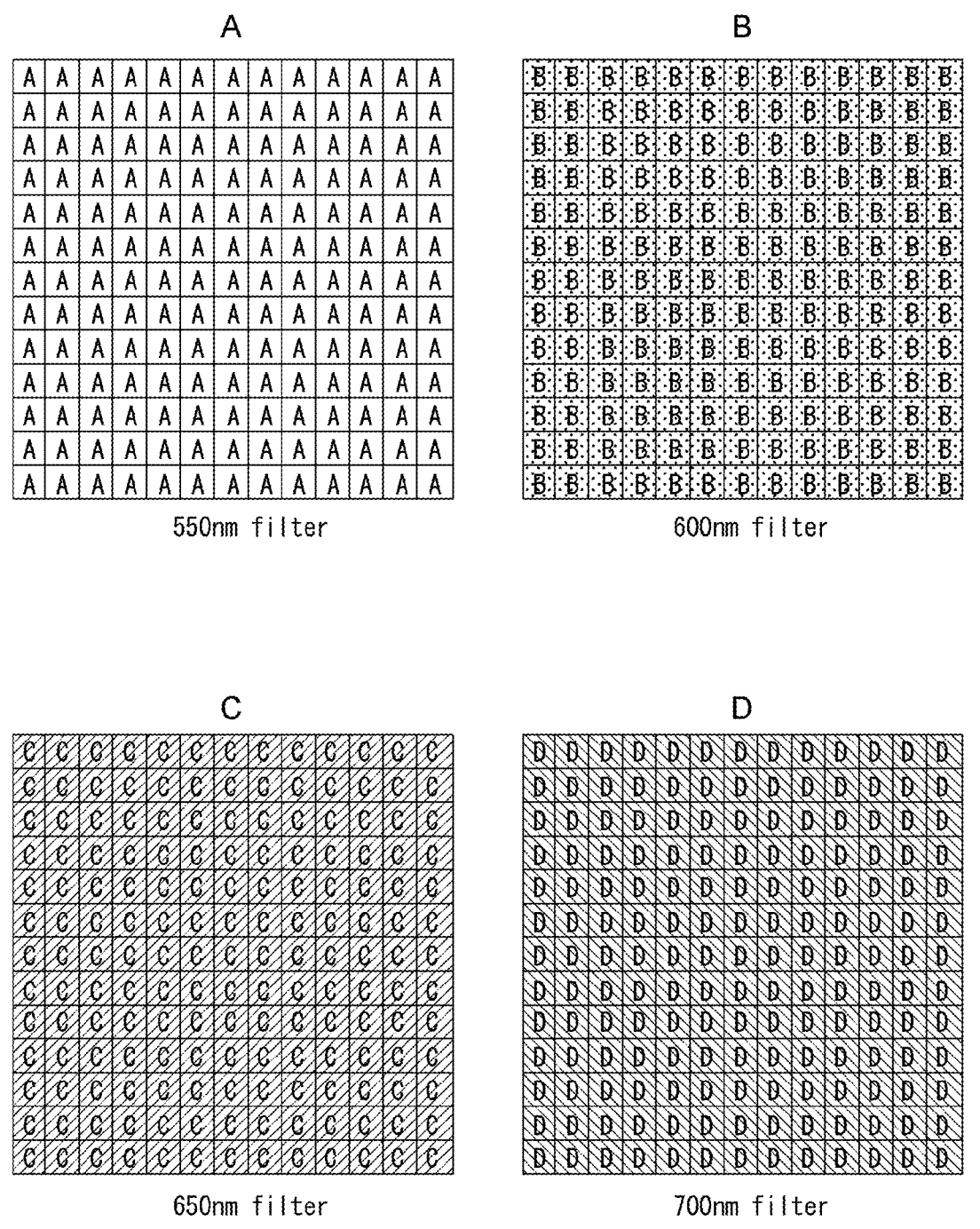

FIG. 11 illustrates a configuration example corresponding to a case of using a plurality of SPAD sensors 10.

As illustrated in each of FIGS. 11A, 11B, 11C, and 11D, the SPAD sensor 10 including only A pixels (550 nm), the SPAD sensor 10 including only B pixels (600 nm), the SPAD sensor 10 including only C pixels (650 nm), and the SPAD sensor 10 including only D pixels (700 nm) are used. In this case, an optical system is configured to disperse the return light from the flow cell 5 side and guide the return light to a light receiving surface of each SPAD sensor 10.

Figures 12, 13:
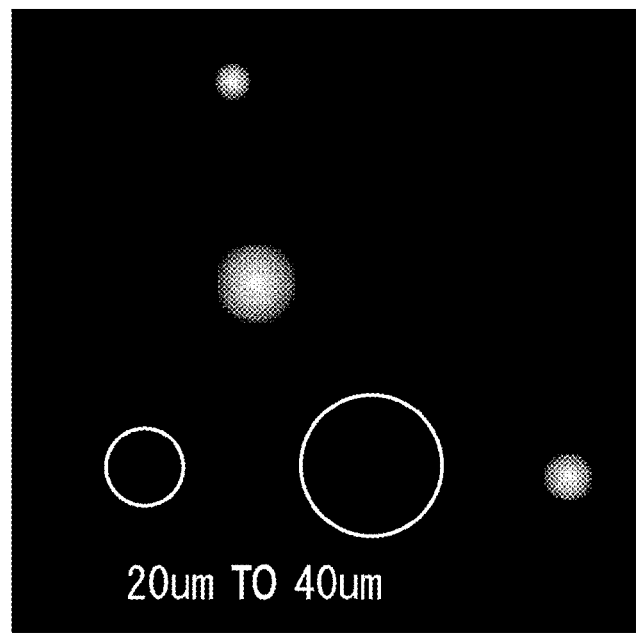
FIG. 12 is a view schematically illustrating an example of a light reception image by the SPAD sensor.
FIG. 13 is an explanatory diagram of an example of detection processing in a case of using the sensor of FIG. 10.

FIG. 12 schematically illustrates an example of a light reception image by the SPAD sensor 10. In the drawing, white hazy and substantially circular portions (three portions in the illustrated example) schematically represent light receiving portions. Furthermore, in the drawing, a correspondence relationship between the size of the light receiving surface of the SPAD sensor 10 and the actual size of the object is illustrated by two white circles. Specifically, the small white circle represents the size of 20 μm, and the large white circle represents the size of 40 μm.

Here, the light reception image illustrated in FIG. 12 illustrates a light reception image by the SPAD sensor 10 without a wavelength filter.

FIG. 13 illustrates an example of the light receiving reaction pixels (represented in black in the drawing) in a case where a light receiving operation is performed for the same object as in the case of FIG. 12 for the SPAD sensor 10 in which the A, B, C, and D pixels are mixedly arranged as illustrated in FIG. 10 above.

FIG. 13 illustrates a case where the light receiving reaction occurs at three points similar to in the case of FIG. 12 as the light receiving operation is performed for the same object as in the case of FIG. 12.

Here, for example, in a case where the definition information I1 illustrated in FIG. 8 is set as the definition information I1 of the target object, the size of the target object is 20 nm to 40 nm, and the wavelength component is 650 nm±10 nm. In the drawing, the light reception reaction is obtained in each of the single B pixel and the single D pixel, but these light receiving reaction regions are different from the wavelength condition in the definition information I1 and do not satisfy the condition of a plurality of adjacent pixels, and thus are not determined as the light receiving region of the target object.

Meanwhile, in the drawing, there is a region in which a light receiving reaction is obtained in a plurality of adjacent C pixels (wavelength: 650 nm). Specifically, the light receiving reaction region of the C pixels is a region of 3×3=9 pixels. Here, for the sake of description, the region for 3×3=9 pixels is assumed to be a region having a size from 20 to 40 μm, both inclusive, in actual object size conversion.

As described above, in the case where the light receiving reaction region satisfies the condition that the light receiving reaction region is a region of a plurality of adjacent pixels and satisfies the condition of the size and wavelength component defined in the definition information, the light receiving reaction region is determined to be the light receiving region of the target object.

Such determination of the light receiving region of the target object can be similarly performed in the case of using the plurality of SPAD sensors 10 as illustrated in FIG. 11 above.

Specifically, in the case of performing the light receiving operation for the same object as in the case of FIG. 12, the light receiving reaction as illustrated in FIG. 14 is obtained in each SPAD sensor 10, but the light receiving reaction region in the SPAD sensor 10 of only the B pixel and the light receiving reaction region in the SPAD sensor 10 of only the D pixel are different from the wavelength condition in the definition information I1 and do not satisfy the condition of a plurality of adjacent pixels, and thus are not determined as the light receiving region of the target object.

As for the light receiving reaction region in the SPAD sensor 10 of only the C pixels, when the region size of 2×2=4 pixels illustrated in the drawing is a size from 20 to 40 μm, both inclusive, in the actual object size conversion, the condition of the size and wavelength in the definition information I1 is satisfied, and the condition of a plurality of adjacent pixels is also satisfied, so that the light receiving reaction region can be determined as the light receiving region of the target object.

Hereinafter, the light receiving region (light receiving reaction region) of the target object determined according to the condition based on the definition information I1 as described above is referred to as "light receiving region Ats".

Note that FIGS. 10 and 11 illustrate the example of providing the wavelength filters in all the pixels of the SPAD sensor 10. However, some pixels without the wavelength filters may be mixed.

In the present example, the imaging operation by the imaging sensor 11 is performed in response to the specification of the light receiving region Ats on the basis of the light reception image by the SPAD sensor 10 as described above (that is, recognition of the presence of an object matching the size/wavelength condition of the target object).

At this time, in the case where the definition information I1 includes image data of the target object as illustrated in FIG. 8, determination as to whether or not the object is the target object is performed on the basis of the captured image by the imaging sensor 11 and the image data.

Figure 15:
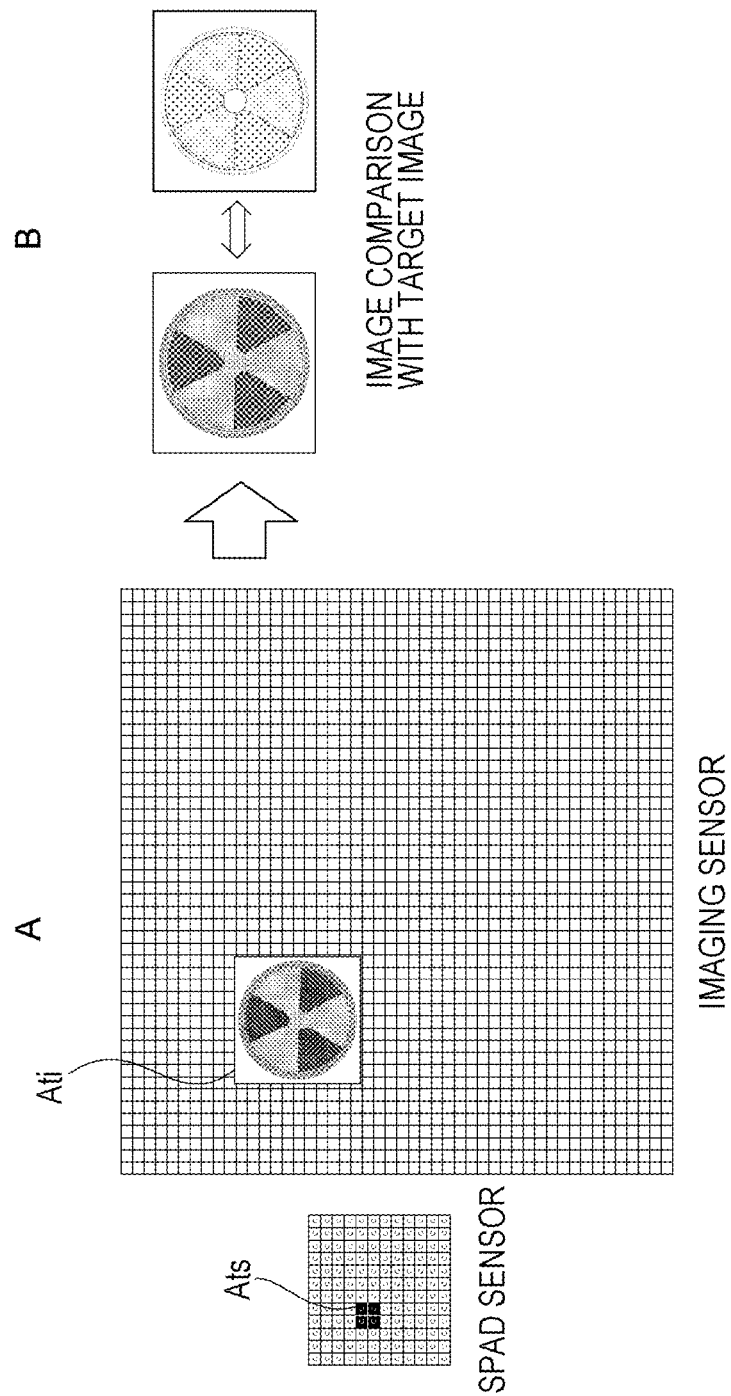
FIG. 15 is a diagram for describing processing of determining a target object based on a captured image in the embodiment.

FIG. 15 is a diagram for describing such processing of determining the target object based on the captured image.

FIG. 15A illustrates a relationship between the light receiving region Ats on the SPAD sensor 10 and an imaging region Ati on the imaging sensor 11. Here, the imaging region Ati means a pixel region of the imaging sensor 11 that can capture the same object as the object captured in the light receiving region Ats.

In the target object determination processing based on the captured image, the image of the imaging region Ati specified from the light receiving region Ats is compared with the target image data (that is, the image data included in the definition information) as illustrated in FIG. 15B. If matching with the image data is confirmed as a result of the image comparison, a final determination result that the object captured in the imaging region Ati (that is, the object captured in the light receiving region Ats) is the target object is obtained.

In the present example, the imaging operation based on predetermined measurement setting information 12 is performed for the object determined to be the target object.

The measurement setting information 12 is information defining various conditions related to the measurement of the target object. Specifically, the measurement setting information 12 of the present example includes the following each information. That is, "measurement execution condition", "sample injection rate", "imaging rule", and "illumination setting" are included.

The "measurement execution condition" is information defining a condition related to execution of measurement, and is, for example, information such as "measurement for 10 minutes at every depth of 200 m" or "measurement for 5 minutes at electrical conductivity of 80 mS/cm or more".

Here, the electrical conductivity is an index of the content degree of mineral in water. The electrical conductivity can be used to investigate a relationship between the mineral content and microorganisms that inhabit the water, and for example, in a case of measuring the microorganisms in a portion having a large amount of minerals, the condition of electrical conductivity as in the above example is set.

In the case of using the electrical conductivity as the measurement condition, a sensor for detecting electrical conductivity of seawater or lake water is externally attached to the measuring device 1. Detection information by the externally attached sensor is input to the control unit 16 via the communication unit 18 illustrated in FIG. 2.

The "sample injection rate" is information defining an injection rate of the sample into the flow cell 5, and is, for example, information such as "0.5 ml/min".

The "imaging rule" is information defining a rule related to imaging of the target object using the imaging sensor 11, and is, for example, information such as "still image imaging" or "moving image imaging". Here, the imaging rule of a moving image can also be information for designating an end condition and a frame rate of moving image imaging, for example, "imaging is performed at 20 fps until the target object comes out of the flow cell 5".

The "illumination setting" is information defining illumination used at the time of imaging the target object using the imaging sensor 11, and is definition information regarding the front light source 7 and the back light source 8 described above in the present example. For example, the illumination setting is information such as "dark field of view imaging (front light source 7)" and "bright field of view imaging (back light source 8)". Note that both the front light source 7 and the back light source 8 can be used for illumination at the time of imaging.

Such measurement setting information 12 is stored in, for example, the storage unit 17, and the measuring device 1 measures the target object according to the measurement setting information 12.

Here, the measuring device 1 performs imaging using the imaging sensor 11 at timing triggered by detection of the target object on the basis of the light reception signal by the SPAD sensor 10, thereby reducing the power consumption related to imaging. In the present example, to further reduce the power consumption, the imaging operation of the target object is performed only for the imaging region Ati.

Specifically, in the example of FIG. 15, regarding the imaging operation started in response to the specification of the light receiving region Ats on the basis of the light reception image by the SPAD sensor 10, the imaging operation using only the imaging region Ati obtained from the light receiving region Ats is performed instead of performing the imaging operation using all the pixels of the imaging sensor 11.

Thereby, the imaging operation for measurement is performed only for a necessary part of the pixel range, and the power consumption can be reduced.

By the way, the measurement of the target object is a concept including the specification of the number, type, and feature of target objects as described above, whereas in appropriately specifying (counting) the number of target objects for each type, appropriate management of counted target objects and uncounted target objects is important for the target objects detected in the imaging field of view.

Therefore, in the present example, the target object once recognized is tracked until the target object is out of the imaging field of view so as to avoid redundant counting.

Figure 16:
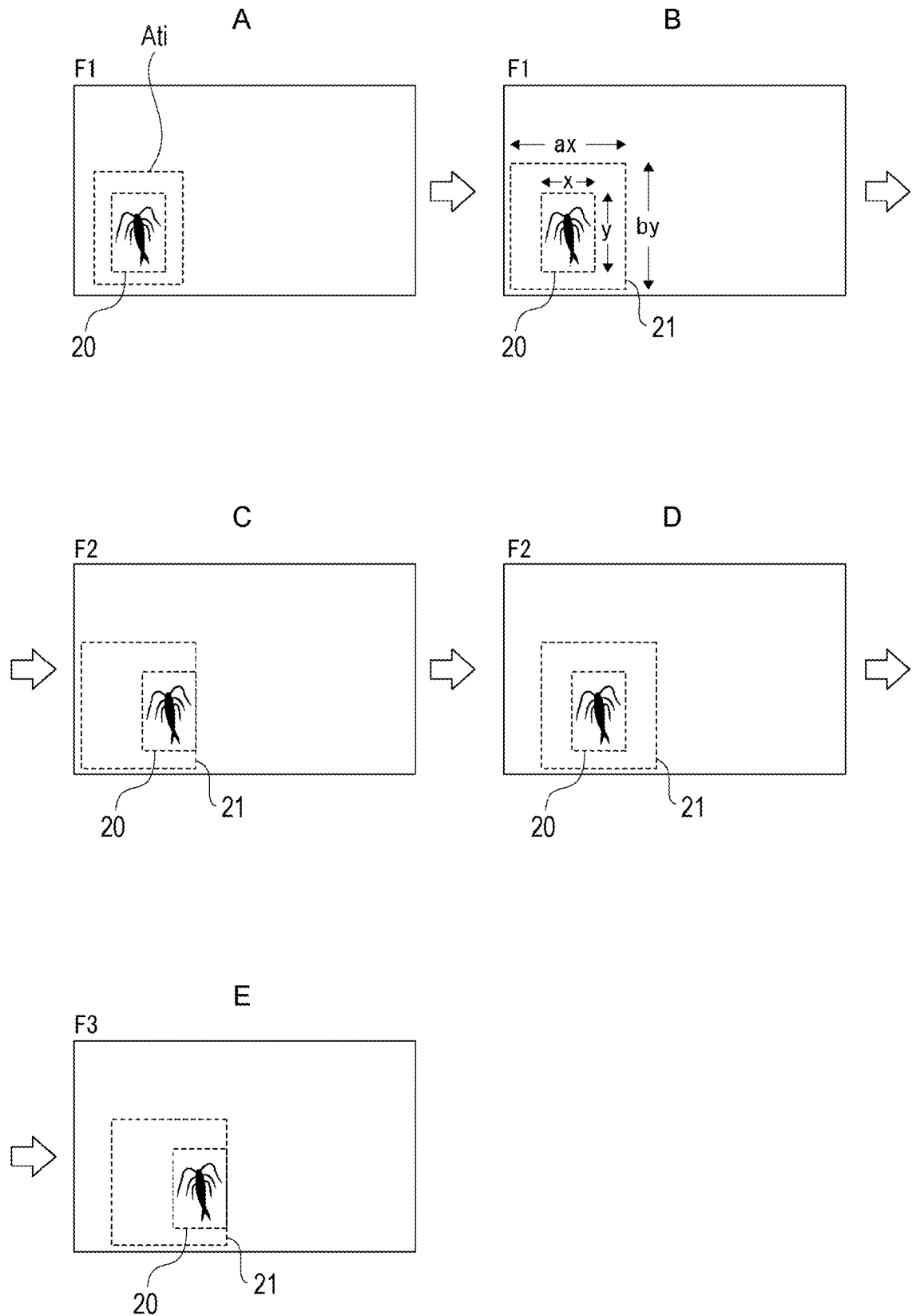
FIG. 16 is an explanatory diagram of tracking of a target object in the embodiment.

FIG. 16 is an explanatory diagram of tracking of the target object in the embodiment.

First, a frame F1 illustrated in FIG. 16A means a frame at a stage where the imaging region Ati is specified from the light receiving region Ats as described with reference to FIG. 15A. As understood from the above description, in the frame F1, the imaging operation is performed only for the imaging region Ati. Then, as described with reference to FIG. 15B, the image comparison (image matching) with the image data in the definition information I1 is performed for the image of the imaging region Ati.

In the case where the target object is recognized by this image matching, a bounding box 20 as a range surrounding the area of the target object is calculated, as illustrated in FIG. 16A.

Then, when the bounding box is calculated, a region of interest (ROI) 21 based on the bounding box is calculated, as illustrated in FIG. 16B.

The ROI 21 is calculated by enlarging (ax×by) horizontal and vertical sizes (x×y) of the bounding box 20. Enlargement scales a and b can be separately set in the vertical and horizontal directions, and an enlargement ratio may be fixed or variable.

A frame F2 illustrated in FIG. 16C is a next frame of the frame F1.

For the frame F2, the imaging operation is performed only for the ROI 21 calculated in the frame F1 that is the previous frame. At this time, assuming that the target object gradually moves in the right direction of the paper surface, the position of the target object in the frame F2 is shifted in the right direction of the paper surface from the position in the frame F1. At this time, the ROI 21 is calculated as a range obtained by enlarging the horizontal and vertical sizes of the bounding box 20, so that the target object can be captured in the ROI 21 in the frame F2 as illustrated in the drawing.

In the frame F2, for example, recognition processing for the target object in the image is performed by performing an image analysis based on the image data of the definition information I1 for the captured image of the ROI 21 calculated in the previous frame, and the bounding box 20 of the target object is calculated.

Then, in the frame F2, the ROI 21 is calculated for the newly calculated bounding box 20 (FIG. 16D).

In a frame F3 illustrated in FIG. 16E, the imaging operation is performed only for the ROI 21 calculated in the frame F2 as described above. Also in this case, since the ROI 21 is a range obtained by enlarging the horizontal and vertical sizes of the bounding box 20, the target object can be captured in the ROI 21 even in the case where the target object moves in a certain direction.

Although not illustrated, in and after the frame F3, the target object recognition processing is performed by performing the image analysis for the captured image of the ROI 21 calculated in the previous frame, the bounding box 20 of the recognized target object is calculated, and the ROI 21 is calculated on the basis of the calculated bounding box 20.

The above-described tracking method can be rephrased as the following method. That is, the bounding box 20 as the range surrounding the target object is set and the ROI 21 that is the region including the bounding box 20 and larger in size than the bounding box 20 is set in the reference frame (the frame F1 in the present example) that is a predetermined frame when or after the target object is detected on the basis of the light reception signal by the SPAD sensor 10, and moreover, the bounding box 20 of the target object is set in the ROI 21 set in the previous frame and the ROI 21 based on the bounding box 20 is set in a frame after the reference frame.

By such a method, it is possible to track the target object even in the case where the target object moves in the captured image.

At this time, the captured image required in each frame for tracking the target object is only the captured image of the ROI 21. Therefore, in the present example, the imaging operation is performed in each frame only for the ROI 21 calculated in the previous frame, as described above. Thereby, it is possible to reduce the power consumption related to imaging for tracking in a case of tracking the target object to prevent erroneous counting.

Note that, in the above description, the example of setting a rectangular region obtained by expanding the bounding box 20 as the ROI 21 has been described. However, the ROI 21 is not limited to the rectangular region.

For example, the ROI 21 by a shape other than a rectangle may be calculated using semantic segmentation, that is, an object area detection result at pixel level.

Here, in the measuring device 1, processing related to cleaning of the flow cell 5 using the cleaning liquid stored in the cleaning liquid container 3 illustrated in FIG. 2 is also performed, which will be described again with reference to the flowchart of FIG. 19.

3. Processing Procedure

Next, an example of a specific processing procedure to be executed for implementing the measuring method as the embodiment described above will be described with reference to the flowcharts of FIGS. 17 to 19.

Figure 17:
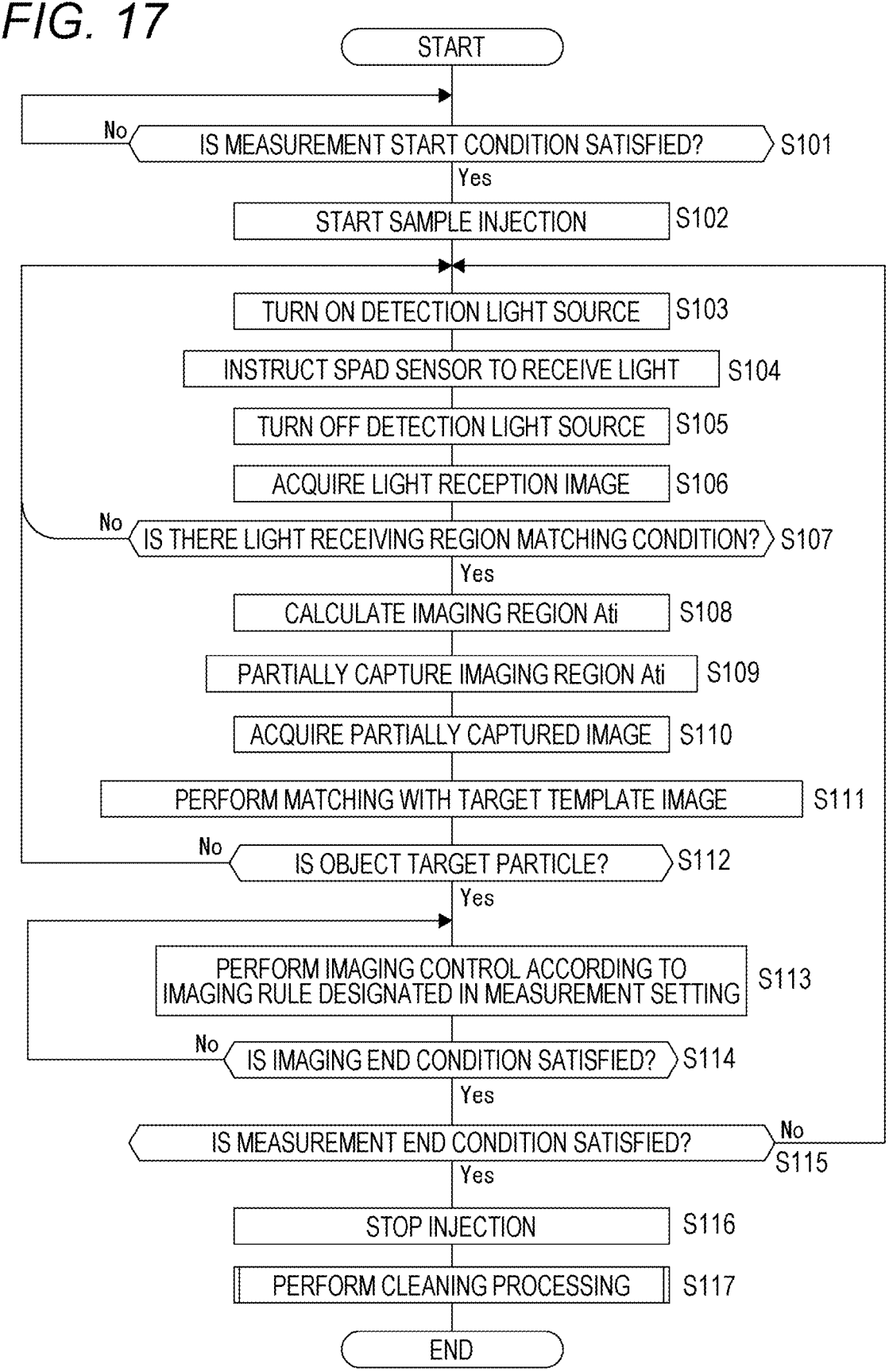
FIG. 17 is a flowchart illustrating a flow of processing from measurement start to measurement end in the embodiment.

FIG. 17 is a flowchart illustrating a flow of processing from measurement start to measurement end. Note that the processing illustrated in FIGS. 17 to 19 is executed by the control unit 16 illustrated in FIG. 2 on the basis of a program stored in a predetermined storage device such as a built-in ROM.

In FIG. 17, in step S101, the control unit 16 waits for satisfaction of measurement start condition. That is, the control unit 16 waits until the condition designated in the "measurement execution condition" in the above-described measurement setting information 12 is satisfied. Note that, in the above description, the case where the conditions of the depth and the electrical conductivity are designated has been exemplified as an example of the "measurement execution condition". The depth and the electrical conductivity are input to the measuring device 1 from an external sensor. Specifically, the information is input via the communication unit 18.

In the case where the measurement start condition is satisfied, the control unit 16 proceeds to step S102 and performs sample injection start processing. That is, by performing control to switch the sample switching unit 4 illustrated in FIG. 2 to the sample container 2 side and giving an instruction to drive the pump in the sample discharge unit 6, injection of the sample into the flow cell 5 is started. At this time, the pump is driven according to the information of the "sample injection rate" in the above-described measurement setting information 12.

In step S103 following step S102, the control unit 16 performs processing of turning ON the detection light source 9, and in next step S104, the control unit 16 instructs the SPAD sensor 10 to receive light. That is, the SPAD sensor 10 is caused to execute the light receiving operation for obtaining one light reception image. Then, in step S105 following step S104, the control unit 16 performs processing of turning OFF the detection light source 9, and in next step S106, the control unit 16 acquires the light reception image.

In step S107 following step S106, the control unit 16 determines whether or not there is a light receiving region (that is, the above-described light receiving region Ats) matching the condition. As understood from the above description, in the present example, not only the condition that the light receiving reaction region can be obtained in a plurality of adjacent pixels, but also the condition of the wavelength and size defined in the definition information I1 is satisfied, the light receiving region Ats is determined.

In step S107, in the case where it is determined that there is no light receiving region matching the condition, the control unit 16 returns to step S103. Thereby, the light irradiation by the detection light source 9 and the light receiving operation by the SPAD sensor 10 are repeatedly executed until the light receiving region Ats is determined.

In step S107, in the case where it is determined that there is a light receiving region matching the condition, the control unit 16 proceeds to step S108 and calculates the imaging region Ati. That is, the imaging region Ati is calculated on the basis of the light receiving region Ats.

Then, in step S109 following step S108, the control unit 16 causes the imaging sensor 11 to execute partial imaging of the imaging region Ati. As the partial imaging, that is, as the imaging operation only for the imaging region Ati, for example, it is conceivable to perform the imaging operation in a form of executing reading of an accumulated charge signal only for a partial pixel range as the imaging region Ati. Alternatively, the partial imaging can be the imaging operation in a form of executing A/D conversion for the charge signal read from each pixel only for some pixels.

In the present embodiment, the imaging operation for the partial pixel range means to perform processing limited to the partial pixel range instead of the entire pixel range for at least some processing from the start of light reception until a captured image signal by a digital signal is obtained.

Note that, regarding the partial imaging in step S109, it is conceivable to control the illumination in accordance with the information of the "illumination setting" in the above-described measurement setting information 12. Alternatively, the illumination control in the partial imaging in step S109 can be performed according to designation information separate from the measurement setting information 12.

In step S110 following step S109, the control unit 16 performs processing of acquiring a partially captured image from the imaging sensor 11, and in next step S111, the control unit 16 matches the partially captured image with the target template image. That is, as described above with reference to FIG. 15B, the image comparison is performed between the partially captured image for the imaging region Ati and the image data in the definition information I1, and the determination processing as to whether or not the object captured in the imaging region Ati is the target object defined in the definition information I1 is performed.

In step S112 following step S111, the control unit 16 determines whether or not the object is a target particle. That is, determination as to whether or not the object captured in the imaging region Ati is the target object is performed on the basis of the result of the matching processing in step S111.

In step S112, in a case where it is determined that the object is not a target particle (that is, not the target object), the control unit 16 returns to step S103. That is, in the case where it is determined that the object captured in the imaging region Ati is not the target object, the light receiving operation by the SPAD sensor 10 is performed again.

On the other hand, in step S112, in a case where it is determined that the object captured in the imaging region Ati is the target object, the control unit 16 proceeds to step S113 and performs imaging control according to the imaging rule designated in the measurement setting. That is, as the control of the imaging sensor 11, control according to the information of the "imaging rule" in the measurement setting information 12 is performed. As described above, as the information of the "imaging rule", for example, information such as "still image imaging" or "moving image imaging", or information such as "imaging is performed at 20 fps until the target object comes out of the flow cell 5" can be set.

Here, the illumination control at the time of the imaging operation executed in step S113 is performed according to the information of the "illumination setting" in the measurement setting information 12.

In step S114 following step S113, the control unit 16 determines whether or not an imaging end condition is satisfied. The imaging end condition here is a condition specified from the information designated as the above-described "imaging rule". For example, in the case of "still image imaging", capturing a still image is the imaging end condition, and in the case of "imaging is performed at 20 fps until the target object comes out of the flow cell 5" regarding moving image imaging, frame-out of the target object from the field of view (imageable range) of the imaging sensor 11 is the imaging end condition.

When the imaging end condition is not satisfied, the control unit 16 executes the processing of step S113 again.

On the other hand, in the case where the imaging end condition is satisfied, the control unit 16 proceeds to step S115 and determines whether or not a measurement end condition is satisfied. The measurement end condition is a condition specified from the information designated as the "measurement execution condition" in the measurement setting information 12. For example, in a case where "measurement for 10 minutes at every depth of 200 m" is specified as the "measurement execution condition", passage of 10 minutes from the satisfaction of the measurement start condition is the measurement end condition.

When the measurement end condition is not satisfied, the control unit 16 returns to step S103.

On the other hand, when the measurement end condition is satisfied, the control unit 16 proceeds to step S116 and executes injection stop processing. That is, the pump of the sample discharge unit 6 is stopped to stop the sample injection into the flow cell 5.

Then, the control unit 16 executes cleaning processing in next step S117 and terminates the series of processing illustrated in FIG. 17.

Note that the cleaning processing in step S117 will be described again.

Figure 18:
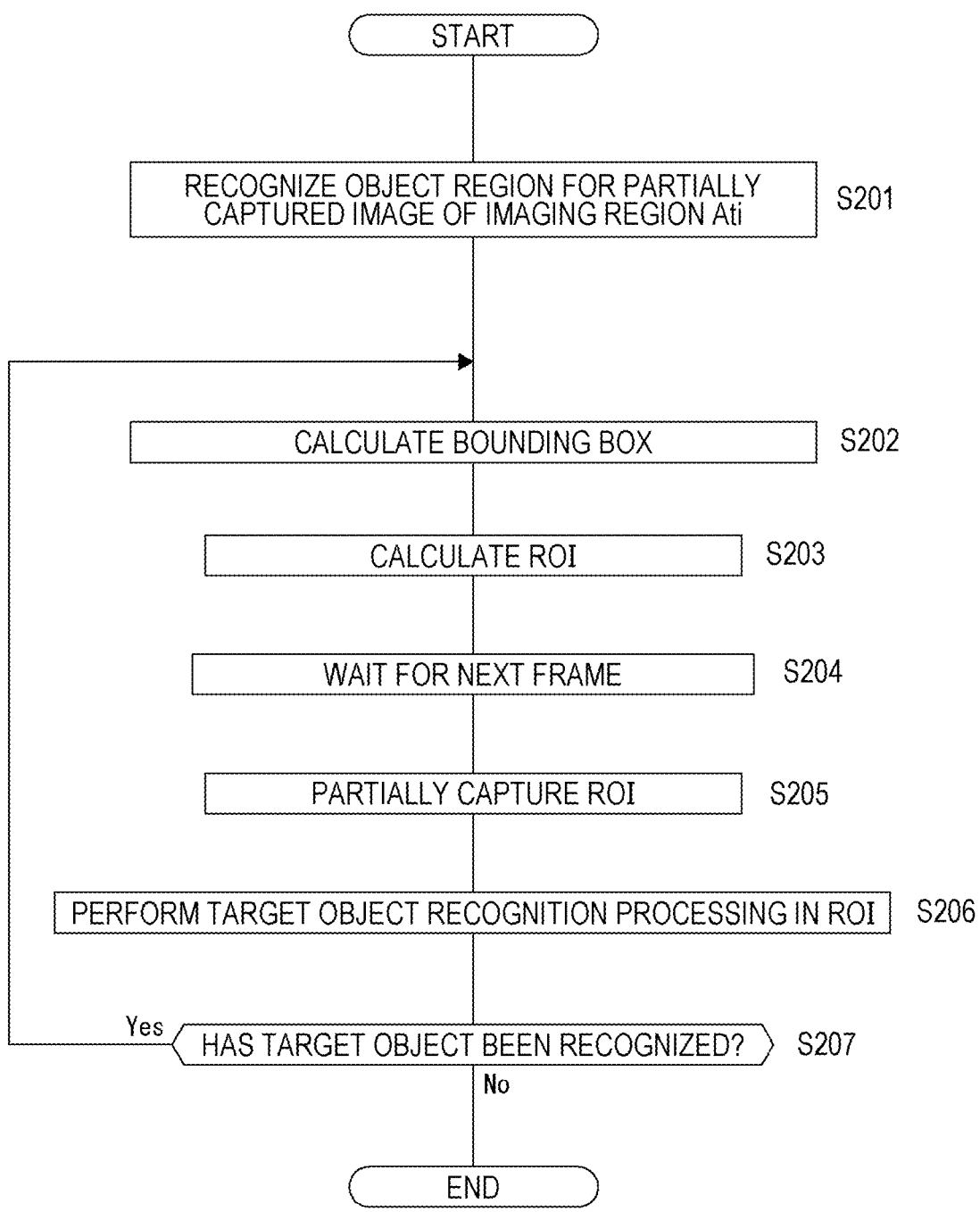
FIG. 18 is a flowchart illustrating a processing procedure for implementing tracking of a target object.

FIG. 18 is a flowchart illustrating a processing procedure for implementing tracking of the target object.

Here, it is conceivable to perform the tracking processing illustrated in FIG. 18 as processing for tracking the target object once recognized until the target object is out of frame so that the counted target object is not redundantly counted when counting the number of target objects in the flow cell 5 as the measurement of the target object.

Alternatively, from the viewpoint of reducing the power consumption related to imaging, it is also conceivable to execute the processing illustrated in FIG. 18 as processing at the time of imaging in a case where the moving image imaging is designated as the "imaging rule".

First, in step S201, the control unit 16 recognizes an object region for the partially captured image of the imaging region Ati. The partially captured image of the imaging region Ati acquired in step S110 of FIG. 17 is used. In the processing of step S201, the region of the target object captured in the partially captured image is recognized.

In step S202 following step S201, the control unit 16 calculates the bounding box 20. That is, the bounding box 20 described in FIG. 16 is calculated on the basis of the region of the target object recognized in the partially captured image.

In step S203 following step S202, the control unit 16 calculates the ROI 21 and waits for the next frame in step S204.

After waiting for the next frame in step S204, the control unit 16 causes partial imaging of the ROI 21 to be executed in step S205. That is, the imaging sensor 11 is caused to execute partial imaging of the ROI 21 calculated in step S203.

In step S206 following step S205, the control unit 16 performs target object recognition processing in the ROI 21. That is, the recognition processing for the target object in the partially captured image of the ROI 21 is performed by performing the image analysis based on the image data of the definition information I1 or the like.

In step S207 following step S206, the control unit 16 determines whether or not the target object has been recognized. When the target object has been recognized in step S207, the control unit 16 returns to step S202. Thereby, when the target object is recognized in the ROI 21 calculated in the previous frame, a new bounding box 20 and ROI 21 for the target object are calculated in the next frame.

On the other hand, when the target object is not recognized in step S207, the control unit 16 terminates the series of processing illustrated in FIG. 18.

Note that, here, an example in which the tracking of the target object is terminated in response to the loss of the target object has been described, but it is also possible to resume the tracking in a case where the target object is recognized again within a predetermined frame from the loss.

Note that, although FIG. 18 illustrates the processing for one target object, in a case corresponding to a plurality of target objects, the processing of steps S201 to S207 is only required to be executed for each target object for which the light receiving region Ats has been specified.

Furthermore, in the processing of FIG. 17, the target object that has not been captured in the imaging field of view at a certain point of time may be captured in the imaging field of view at another point of time thereafter because the sample moves in a certain direction in the flow cell 5, and it is also conceivable to perform processing capable of coping with such a situation. Specifically, in that case, it is conceivable to execute the processing of steps S103 to S107, for example, at regular time intervals after the start of sample injection in step S102. In a case where a new light receiving region Ats is specified, an imaging region Ati corresponding to the light receiving region Ats is specified, and partial imaging is performed for the imaging region Ati.

Figure 19:
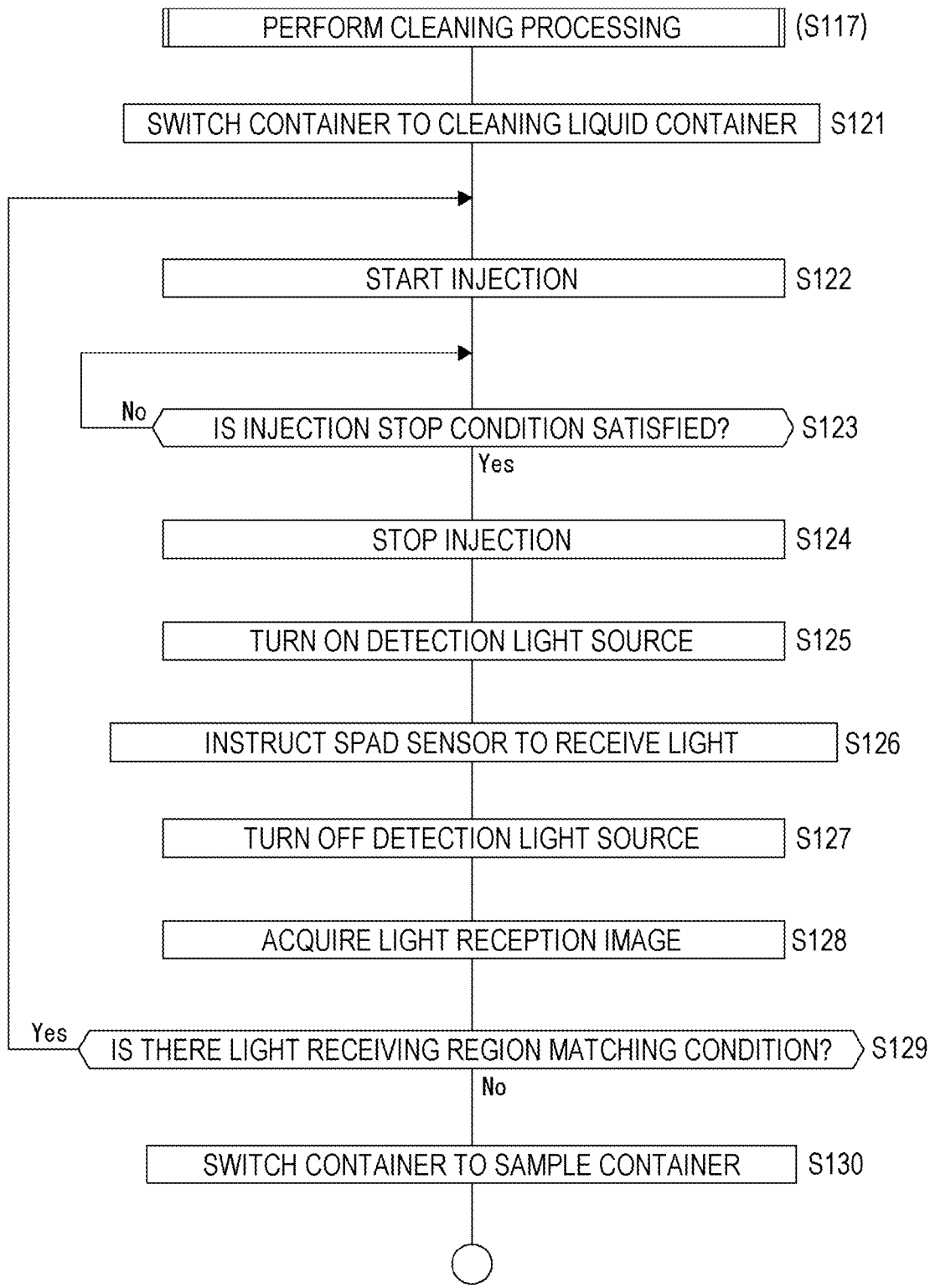
FIG. 19 is a flowchart of cleaning processing (S117) in FIG. 17.

FIG. 19 is a flowchart of the cleaning processing (S117) illustrated in FIG. 17.

First, in step S121, the control unit 16 performs processing of switching the container to the cleaning liquid container 3. That is, the control unit 16 instructs the sample switching unit 4 to switch the container from the sample container 2 to the cleaning liquid container 3.

In step S122 following step S121, the control unit 16 drives the pump of the sample discharge unit 6 to start the injection of the cleaning liquid from the cleaning liquid container 3 into the flow cell 5 as the injection start processing, and waits for satisfaction of the injection stop condition in next step S123. As the injection stop condition here, a condition such as passage of a certain time from the start of injection or injection of a predetermined amount or more of the cleaning liquid into the flow cell 5 is conceivable, for example. Note that the condition related to cleaning such as an injection stop condition may be variably set by setting information such as the measurement setting information 12.

In the case where the injection stop condition is satisfied, the control unit 16 performs processing of stopping the driving of the pump of the sample discharge unit 6 as the injection stop processing of step S124, and advances the processing to step S125.

Steps S125 to S128 are processing for obtaining the light reception image by the SPAD sensor 10 for the flow cell 5 after cleaning. First, the control unit 16 turns ON the detection light source 9 in step S125, instructs the SPAD sensor 10 to receive light in step S126, and turns OFF the detection light source 9 in step S127. Then, in next step S128, the control unit 16 acquires the light reception image by the SPAD sensor 10.

In step S129 following step S128, the control unit 16 determines whether or not there is a light receiving region matching the condition. That is, whether or not there is a light receiving region Ats matching the condition of the wavelength and size designated in the definition information I1 in the light reception image. This corresponds to determining whether or not an object corresponding to the target object remains in the flow cell 5.

In step S129, in the case where there is a light receiving region matching the condition, the control unit 16 returns to step S122. Thereby, in a case where an object remains in the flow cell 5 after cleaning, the flow cell 5 is cleaned again.

On the other hand, in a case where it is determined in step S129 that there is no light receiving region meeting the condition, the control unit 16 proceeds to step S130 and executes the processing of switching the container to the sample container 2, and then terminates the series of processing illustrated in FIG. 19.

Here, although not illustrated, it has been described that the number and the size are specified for the measurement of the target object, but the measurement may be processing of specifying the feature of the target object. For example, in the case of the target object=plankton, it is conceivable to specify a shape feature (presence or absence and number of flagella, cilia, tactile sense, foot, eye, or body segment) or a structural feature (presence or absence of cells, distinction between single cells and multiple cells, presence or absence of movement, presence or absence of chloroplasts, or the like) by image analysis of the captured image.

Furthermore, in the measurement, the specified information can be stored in the storage unit 17 or the like as measurement result information. For example, it is conceivable to store feature information regarding the shape and structure as described above. Furthermore, in the light reception image by the SPAD sensor 10, return light (fluorescence, reflection, or scattering light) from the target object is detected, but it is also conceivable to store information indicating a wavelength component of the return light.

Furthermore, the storage of the measurement result can be performed for each type of the specified target object.

Moreover, detection information by an external sensor can be stored together with the information of these measurement results. For example, in the case of using the depth and electrical conductivity information described above, it is conceivable to store external sensor information together with the measurement result information.

4. Sensor Structure

Figure 20:
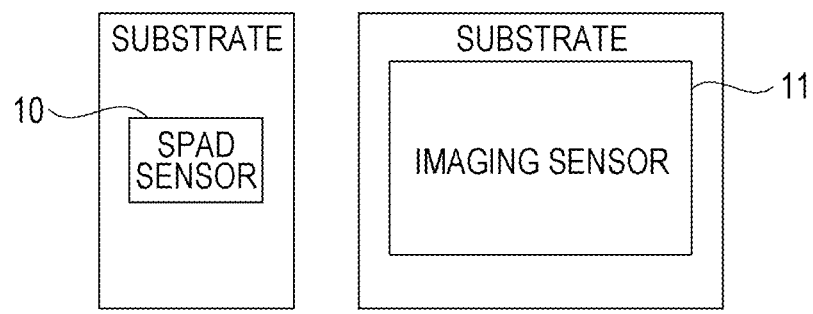
FIG. 20 is an explanatory diagram of an example in which the SPAD sensor and an imaging sensor are formed on separate substrates.
Figure 21:
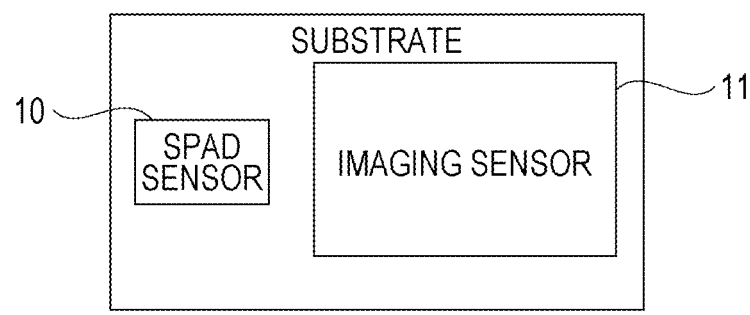
FIG. 21 is an explanatory diagram of an example in which the SPAD sensor and the imaging sensor are formed on a common substrate.
Figure 22:
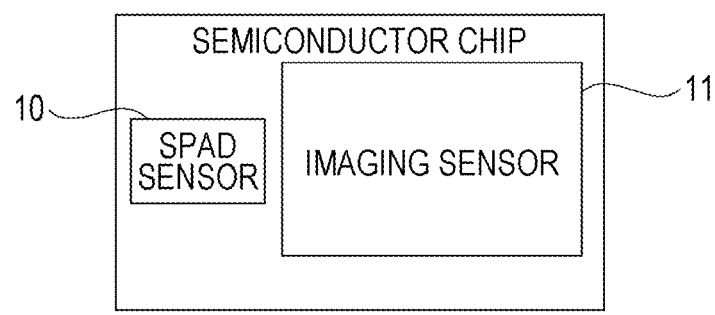
FIG. 22 is an explanatory diagram of an example in which a functional unit as the SPAD sensor and a functional unit as the imaging sensor are formed in a common semiconductor chip.

The SPAD sensor 10 and the imaging sensor 11 can have structures illustrated in FIGS. 20 to 22.

FIG. 20 illustrates an example in which the SPAD sensor 10 and the imaging sensor 11 are formed on separate substrates.

FIG. 21 illustrates an example in which the SPAD sensor 10 and the imaging sensor 11 are formed on a common substrate.

FIG. 22 illustrates an example in which a functional unit as the SPAD sensor 10 and a functional unit as the imaging sensor 11 are formed in a common semiconductor chip.

Here, in the case where the SPAD sensor 10 and the imaging sensor 11 are formed on separate substrates as illustrated in FIG. 20, it is not necessary to arrange the SPAD sensor 10 and the imaging sensor 11 in parallel (arrangement in which light receiving surfaces of the sensors are parallel to each other) in the measuring device 1.

Figure 23:
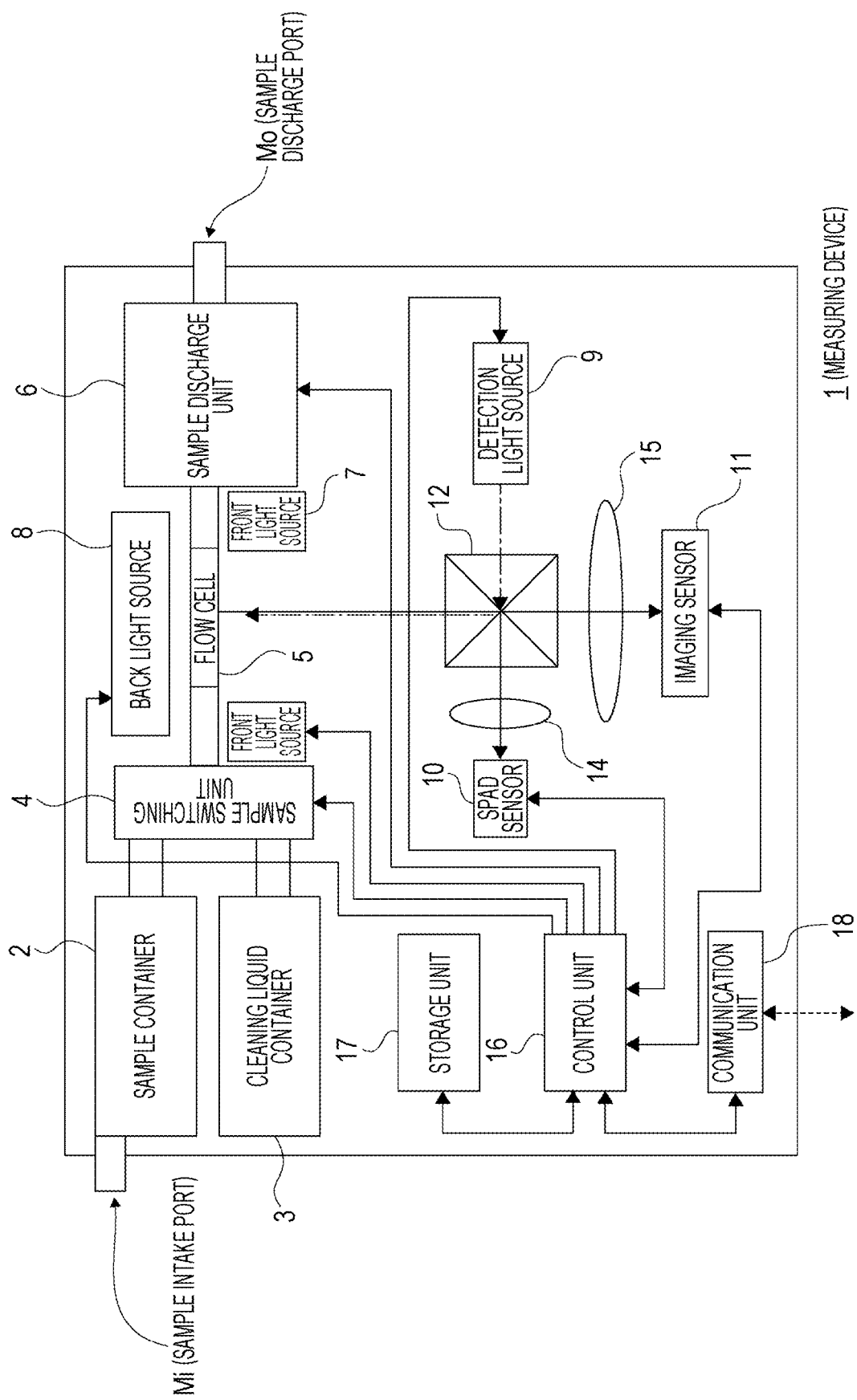
FIG. 23 is a diagram illustrating a configuration example of a measuring device in which a mirror on an optical path of the SPAD sensor is omitted corresponding to the case of adopting the configuration illustrated in FIG. 20.

Therefore, it is possible to adopt a configuration in which the mirror 13 is omitted, as illustrated in FIG. 23.

Furthermore, a single sensor having the function as the SPAD sensor 10 and the function as the imaging sensor 11 (that is, a function to capture the target object on the basis of the control of the control unit 16) can also be used.

Figure 24:
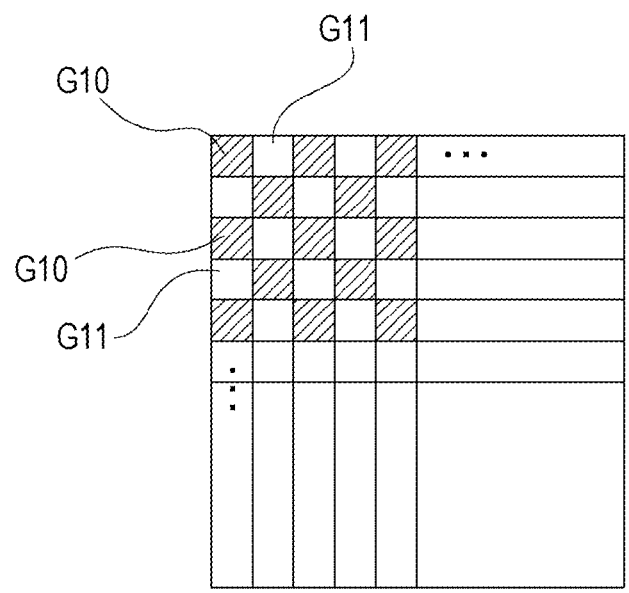
FIG. 24 is an explanatory diagram of an example of a single sensor having a function as the SPAD sensor and a function as the imaging sensor.
Figure 25:
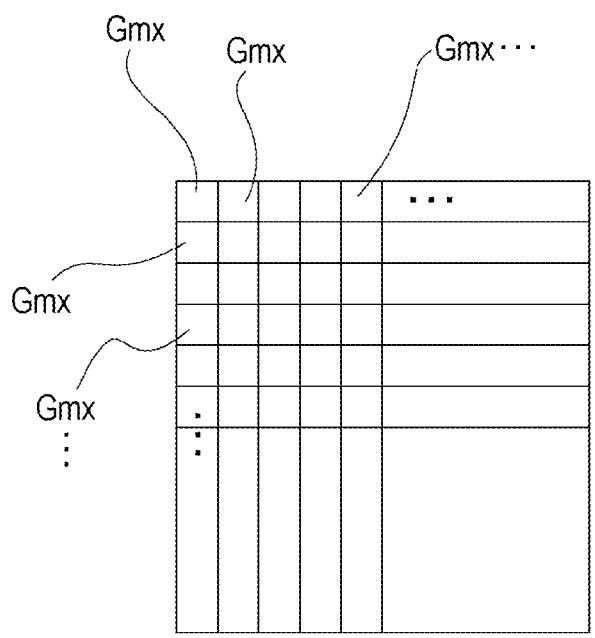
FIG. 25 is an explanatory diagram of another example of the single sensor having a function as the SPAD sensor and a function as the imaging sensor.

FIGS. 24 and 25 illustrate examples of such a single sensor.

In the example of FIG. 24, a pixel G10 having a SPAD element as a photoelectric conversion element and a pixel G11 used in the imaging sensor 11 are mixed in a same pixel array unit. Here, the pixel G11 can be rephrased as a pixel including a photoelectric conversion element having a lower light receiving resolution than the SPAD element.

The example of FIG. 25 is an example of using a pixel Gmx having both the function of the pixel G10 and the function of the pixel G11 described above. In the sensor in this case, a plurality of pixels Gmx is two-dimensionally arrayed as illustrated in the drawing.

Here, the pixel Gmx can be rephrased as a pixel including, as a photoelectric conversion element, a photoelectric conversion element capable of performing both light amount detection with a resolution in units of photons and light amount detection with a resolution in normal imaging.

In the case where the SPAD sensor 10 and the imaging sensor 11 are separated as in the examples of FIGS. 22 and 21, existing sensors can be used as the sensor functioning as the light receiving unit (the sensor that performs photoelectric conversion using an electron avalanche phenomenon) and the imaging sensor that captures the target object, respectively. Therefore, it is not necessary to develop and use a new sensor, and in this respect, the cost of the measuring device 1 can be reduced.

Meanwhile, in the case where the sensor is configured as a single sensor as in the examples of FIGS. 24 and 25, it is not necessary to provide a spectroscopic means (half mirror 12), which is required in the case where the sensors are separated, and thus, it is possible to reduce the number of components of the optical component and to reduce the size of the measuring device 1.

5. Imaging Sensor

Figure 26:
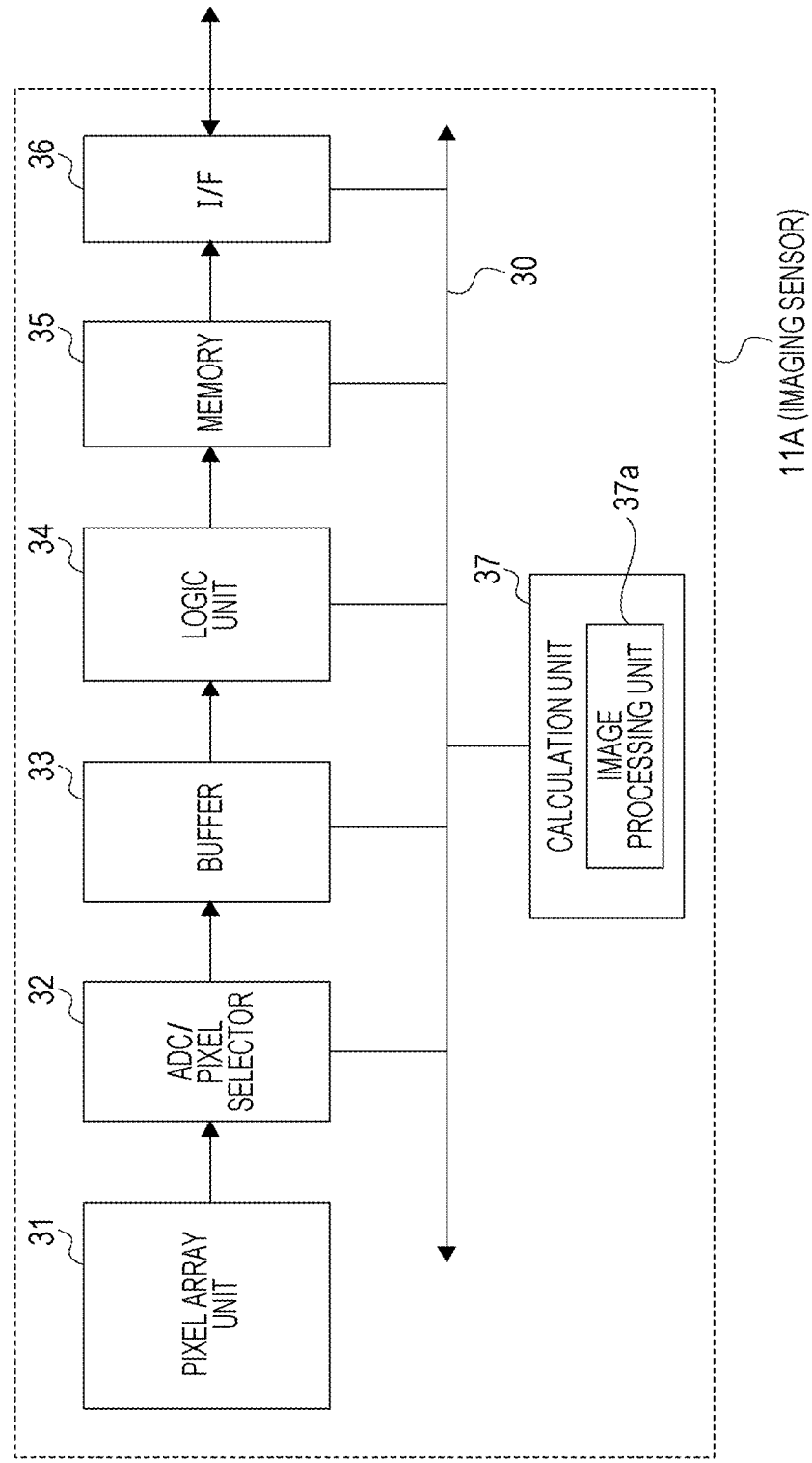
FIG. 26 is a block diagram illustrating an internal configuration example of an imaging sensor as a modification.

FIG. 26 is a block diagram illustrating an internal configuration example of an imaging sensor 11A as a modification.

The imaging sensor 11A has a function to generate captured image data and an image processing function for the captured image data. In particular, the imaging sensor 11A is a device having an object detection function by image analysis and which can be called intelligent array sensor.

As illustrated, the imaging sensor 11A includes a pixel array unit 31, an analog to digital converter (ADC)/pixel selector 32, a buffer 33, a logic unit 34, a memory 35, an interface (I/F) unit 36, and a calculation unit 37.

Each unit of the ADC/pixel selector 32, the buffer 33, the logic unit 34, the memory 35, the interface (I/F) unit 36, and the calculation unit 37 can perform data communication with each other via a bus 30.

The pixel array unit 31 is configured by two-dimensionally arraying a plurality of pixels each having a photoelectric conversion element, such as the above-described pixel G11.

An electrical signal photoelectrically converted by the pixel array unit 31 is input to the ADC/pixel selector 32. The ADC/pixel selector 32 digitizes the electrical signal as an input analog signal and outputs an image signal (image data) as digital data.

Furthermore, the ADC/pixel selector 32 has a function to select a pixel for a pixel (photoelectric conversion element) of the pixel array unit 31. Thereby, a photoelectric conversion signal can be acquired, converted into digital data, and output only for the selected pixel in the pixel array unit 31. That is, the ADC/pixel selector 32 normally digitizes and outputs the photoelectrically converted signal as digital data for all of effective pixels constituting an image of one frame, but also can digitize and output the photoelectrically converted signals of only the selected pixels as digital data.

For example, such an ADC/pixel selector 32 can implement partial imaging for the above-described imaging region Ati.

The ADC/pixel selector 32 acquires the image data in frame units, and the image data of each frame is temporarily stored in the buffer 33, read out at appropriate timing, and used for processing by the logic unit 34.

The logic unit 34 can perform various types of necessary signal processing (image signal processing) for each input frame image signal.

For example, the logic unit 34 can perform image quality adjustment by processing such as color correction, gamma correction, color gradation processing, gain processing, and contour enhancement processing. Furthermore, it is also conceivable that the logic unit 34 performs processing of changing a data size, such as data compression processing, resolution conversion, and frame rate conversion.

Parameters to be used for each processing are set for each processing performed by the logic unit 34. For example, there are setting values such as color or luminance correction coefficients, a gain value, a compression rate, and a frame rate. The logic unit 34 performs necessary processing using the parameters set for each processing. In the present embodiment, the calculation unit 37 may set these parameters.

The image data processed by the logic unit 34 is stored in the memory 35 including, for example, a dynamic random access memory (DRAM) or the like.

The image data stored in the memory 35 is transmitted and output to the outside (for example, the control unit 16) by the interface unit 36 at necessary timing.

The calculation unit 37 includes, for example, a microcomputer including a CPU, a ROM, a RAM, and the like. The calculation unit 37 exchanges instructions and data with respect to each unit of the ADC/pixel selector 32, the buffer 33, the logic unit 34, the memory 35, and the interface (I/F) unit 36 via the bus 30. For example, processing of instructing, to the ADC/pixel selector 32, a pixel range in which the photoelectric conversion signal is to be digitized and output as digital data, is performed. Furthermore, various parameters are instructed to the logic unit 34 as necessary.

Furthermore, the calculation unit 37 has a function as an image processing unit 37a. The image processing unit 37a is, for example, a processing unit having artificial intelligence (AI), and can perform processing of detecting an object in the captured image data and processing of recognizing the detected object.

The term "object" as used herein refers to an object that can be a detection target for the purpose of recognition from an image. What kind of object is to be detected varies depending on the use of the measuring device 1 and the like, but any object may be the object referred to herein. For example, any object such as an animal including a person, a moving object (an automobile, a bicycle, an aircraft, or the like), a natural object (a vegetable, a plant, or the like), an industrial product/part, a building, a facility, a mountain, sea, river, star, sun, cloud, or the like can correspond to the object to be detected although the above are merely examples.

Furthermore, in the object recognition processing by the image processing unit 37a, it is possible to perform class classification for the detection object. Here, the class is information indicating a category of the object, and the object to be classified is classified into, for example, "person", "automobile", "airplane", "ship", "truck", "bird", "cat", "dog", "deer", "frog", or "horse".

Here, the image processing by the calculation unit 37 as exemplified above is processing that is not normally performed in an image sensor. Therefore, it can be said that the imaging sensor 11A performs more intelligent processing than a normal image sensor, and in this sense, can be referred to as an intelligent array sensor.

In the case of using the imaging sensor 11A, at least the processing related to image recognition among the above-described processing of the control unit 16 can be performed on the imaging sensor 11A side.

Specifically, among the processing illustrated in FIG. 17, the matching processing in step S111 and the determination processing in step S112 based on the matching processing can be performed using the image processing unit 37a in the imaging sensor 11A. Furthermore, the target object tracking processing illustrated in FIG. 18 can also be performed using the image processing unit 37a.

Here, in the case of performing the above processing using the image processing unit 37a, the image data used for the target object recognition processing is stored in a storage device (for example, the memory 35) in the imaging sensor 11A.

Furthermore, in the case of performing the processing of counting the number of the target objects for each type or the processing of extracting the feature information as described above as the measurement of the target object based on the captured image, it is conceivable to perform the processing using the image processing unit 37a. In that case, it is also possible to adopt a configuration in which the measurement result information is stored in a storage device in the imaging sensor 11A, such as the memory 35, for example, and the calculation unit 37 outputs the information via the interface unit 36 in response to a request from the outside (for example, the control unit 16).

Furthermore, in the case of performing the matching processing in step S111 using the image processing unit 37a, matching processing using a class identification function by AI can be performed. In that case, as AI, a plurality of classes such as "phytoplankton" and "zooplankton" is configured to be identifiable as classes of objects. Furthermore, template images to be used in the matching processing are prepared for the respective classes (for example, the template images are stored in the memory 35 or the like). Then, as the matching processing in step S111, the image processing unit 37a performs the class identification processing using AI for the captured image of the imaging region Ati to identify the class of the object captured in the imaging region Ati. Then, a template image corresponding to the identified class is selected, image matching using the selected template image is performed, and determination as to whether or not the object in the imaging region Ati is the target object is performed.

By performing the image matching after narrowing the class in this manner, it is possible to improve the efficiency of the image matching processing.

Note that the matching processing using such class identification can also be performed by the control unit 16.

6. Modification

6-1. First Modification

Here, the embodiment is not limited to the specific examples described above, and configurations as various modifications can be adopted.

For example, in the above description, an organism such as plankton has been mainly exemplified as an example of the target object to be measured, but the target object may be a non-organism. Hereinafter, as an example, a lighting device 1B corresponding to a case of detecting microplastics floating in the seawater or the like as the target object will be described.

Figure 27:
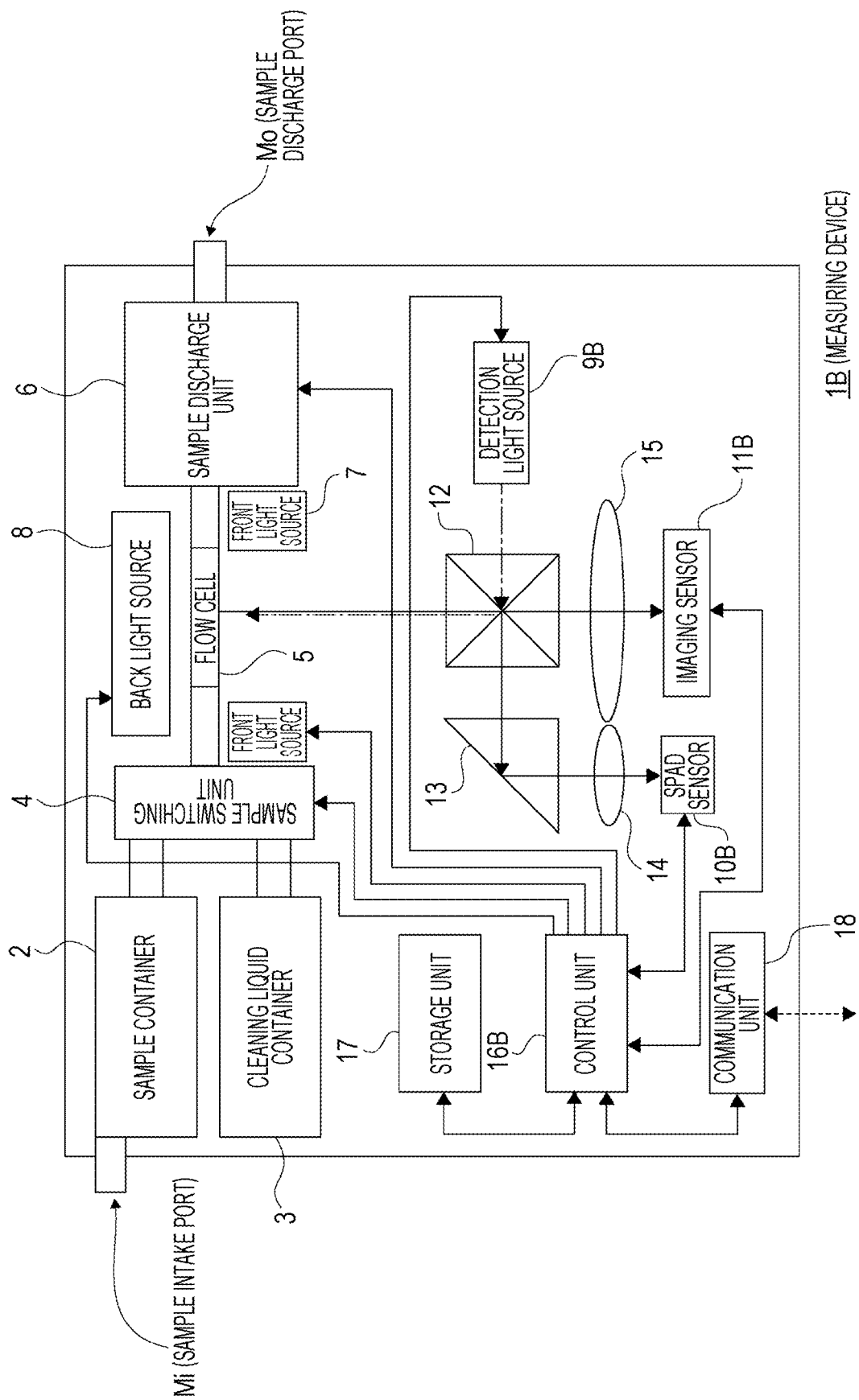
FIG. 27 is a diagram illustrating an internal configuration example of a measuring device as a first modification.

FIG. 27 illustrates an internal configuration example of the lighting device 1B as a modification.

First, as a premise, microplastics floating in the seawater or the like can be roughly classified into a chip type and a fiber type in terms of shape. Then the microplastics of the chip type and the fiber type can be further classified according to their materials. Specifically, examples of the material types of the microplastics include polyethylene, phenol, polycarbonate, polystyrene, and polypropylene. For example, it is possible to distinguish the polyethylene material and the phenol material from each other in the chip type, or distinguish the chip type and the fiber type from each other although they are the same polystyrene material.

These microplastics react to near-infrared light (wavelength of about 780 nm to 2000 nm) (that is, reflected light is generated). Therefore, in detecting the microplastics, a detection light source 9B capable of emitting light including a wavelength component of near-infrared light is used instead of the detection light source 9. Furthermore, as the SPAD sensor 10, a SPAD sensor 10B having sensitivity to near-infrared light is used. Here, the detection light source 9B can be configured by, for example, a tungsten halogen lamp, a semiconductor laser, or the like.

Furthermore, as the imaging sensor 11, an imaging sensor 11B having sensitivity to near-infrared light is used.

Furthermore, in the measuring device 1B, a control unit 16B is provided instead of the control unit 16 in order to detect the microplastics and recognize the target object.

Here, the microplastics have a unique distribution as a power spectrum distribution (distribution of reflected light intensity with respect to wavelength) of the reflected light in a near-infrared region. This unique power spectrum distribution is referred to as a "feature power spectrum".

Therefore, by determining whether or not the power spectrum distribution of the reflected light in the near-infrared region has a distribution as a feature power spectrum of the microplastics for a light receiving reaction portion in the SPAD sensor 10B, it is possible to determine whether or not the light receiving reaction portion is a light receiving reaction portion (light receiving region) of the microplastics.

At this time, to enable detection of the spectral distribution, the SPAD sensor 10B provided with wavelength filters for different wavelengths in the near-infrared region is used. For example, wavelength filters having different wavelengths alternately arranged, as illustrated in FIG. 10, are used.

Furthermore, the pattern of the power spectrum distribution of the reflected light varies depending on the material type of the microplastics. In the present example, the material type determination based on such a pattern of the power spectrum distribution is assumed to be performed on the basis of the captured image of the imaging sensor 11B.

Therefore, similarly to the SPAD sensor 10B, the imaging sensor 11B is configured to be able to identify the difference in wavelength of reflected light for the near-infrared light. Specifically, the wavelength filters having different wavelengths in the near-infrared region alternately arranged are used as in the example of FIG. 10.

With the above premise, processing for measuring the microplastics will be described with reference to the flowchart of FIG. 28.

Note that, in this drawing, it is assumed that the light receiving operation is performed by the SPAD sensor 10B in a state where the detection light source 9B is already turned on, and the light reception image is acquired by the control unit 16.

Figure 28:
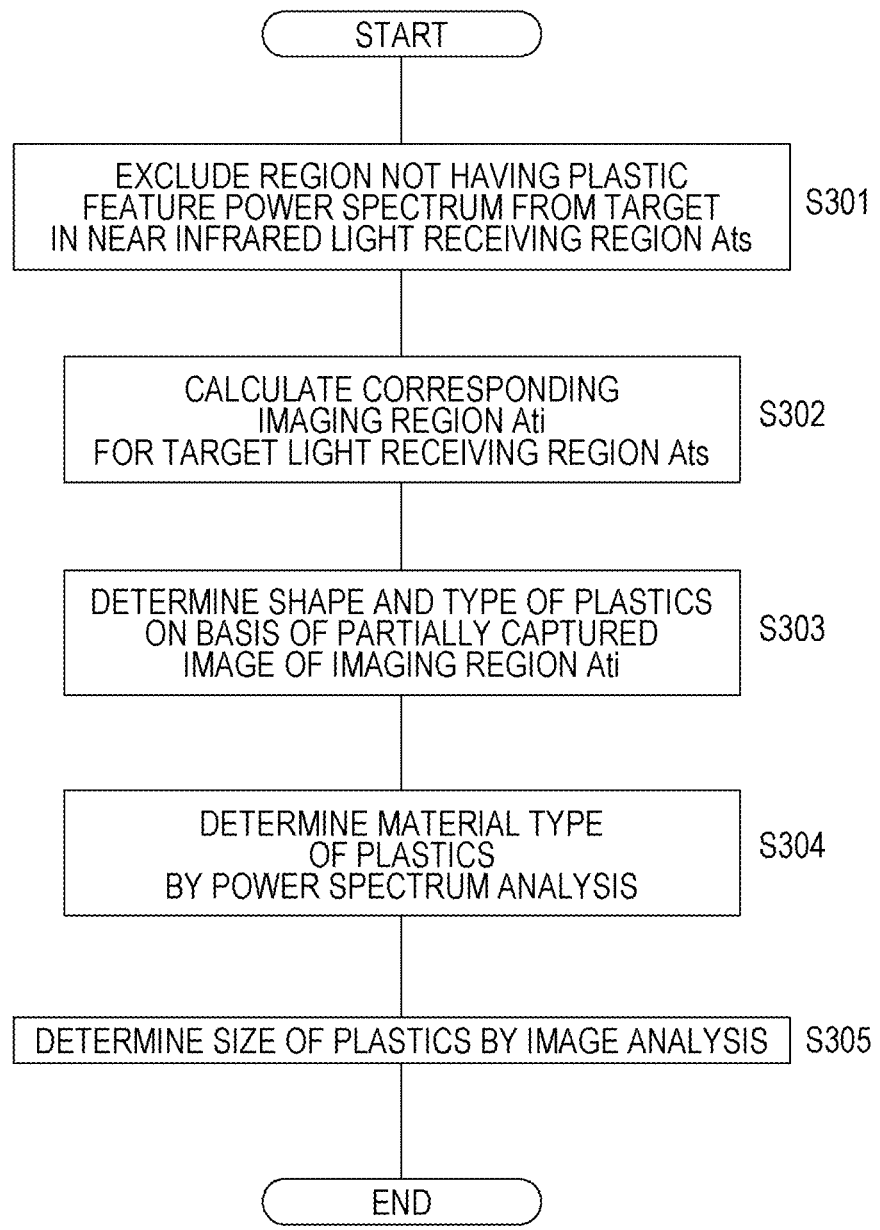
FIG. 28 is a flowchart of processing for measuring microplastic in the first modification.

In FIG. 28, in step S301, the control unit 16B performs processing of excluding a region not having the feature power spectrum of plastics from the target in the light receiving region Ats of the near infrared light. As described above, the SPAD sensor 10B is provided with wavelength filters having different wavelengths in units of pixels in the near-infrared region, and thus can detect reflected light power for each of the different wavelengths in the near-infrared region in the light receiving region Ats in this case. In step S301, it is possible to determine whether or not to have the feature power spectrum of plastics on the basis of such reflected light power for each wavelength.

By excluding the region not having the feature power spectrum of plastics from the target in the near-infrared light receiving region Ats, imaging is not performed for an imaging range corresponding to the light receiving region Ats.

In step S302 following step S301, the control unit 16B calculates the corresponding imaging region Ati for the target light receiving region Ats. That is, the corresponding imaging region Ati is calculated for the light receiving region Ats determined to have the feature power spectrum of plastics in step S301.

Then, in step S303 following step S302, the control unit 16B determines the shape and type of the plastics on the basis of a partially captured image of the imaging region Ati. That is, the chip type and the fiber type described above are determined. Note that it goes without saying that the control unit 16B instructs the imaging unit 11B to execute partial imaging of the imaging region Ati in executing the processing in step S303.

The determination of the shape and type in step S303 can be performed by an image analysis for the partially captured image. For example, the shape type can be determined by matching image data in the definition information I1 set in advance for each target plastic.

In step S304 following step S303, the control unit 16B determines the type of plastic material by a power spectrum analysis. As described above, the imaging sensor 11B is provided with wavelength filters having different wavelengths in units of pixels in the near-infrared region, and thus can detect reflected light power for each of the different wavelengths in the near-infrared region in the imaging region Ati in this case. In step S304, the type of plastic material is determined on the basis of the reflected light power for each wavelength and the feature power spectrum for each plastic material to be set in advance.

In step S305 following step S304, the control unit 16B determines the size of the plastics by an image analysis. For the size determination, it is conceivable to determine the size having a range from 20 to 40 µm, or the like.

The control unit 16B terminates the series of processing illustrated in FIG. 28 in response to the execution of the processing of step S305.

Note that FIG. 28 illustrates the processing related to measurement of microplastics, but processing related to measurement of microorganisms such as plankton can be performed together with the processing of FIG. 28. That is, the processing related to measurement of microorganisms as illustrated in FIG. 17 or FIG. 18 above is also performed.

Here, in a case of measuring both the microorganisms and the microplastics, the wavelength band of the return light from the microorganisms may be close to the wavelength band of the return light from the microplastics depending on the type of the target microorganisms. In such a case, to increase the detection accuracy of the target object, the light receiving region Ats specified as the light receiving region for the microorganisms can be excluded from the detection target of microplastics.

Furthermore, for the measurement based on the captured image, it is also possible to exclude the imaging region Ati in which features of microorganisms are recognized, such as the presence of cilia or flagella, from the measurement target of microplastics.

Note that the tracking processing for the target object as described in FIG. 18 can be also performed in the above-described measuring device 1B as a modification. That is, it is possible to perform the tracking processing for the target object as microplastics.

Furthermore, the imaging sensor 11A described in FIG. 26 can also be applied to the measuring device 1B. In this case, it is conceivable that the shape type determination processing in step S303, the material type determination processing in step S304, and the size determination processing in step S305 are executed by the image processing unit 37a. Furthermore, in the case of performing the tracking processing for the microplastics, the tracking processing can also be executed by the image processing unit 37a.

6-2. Second Modification

In the above description, an example of sampling the seawater as the sample to the flow cell 5 in measuring the target object has been described but it is not essential to use the flow cell 5 in measuring the target object.

Figure 29:
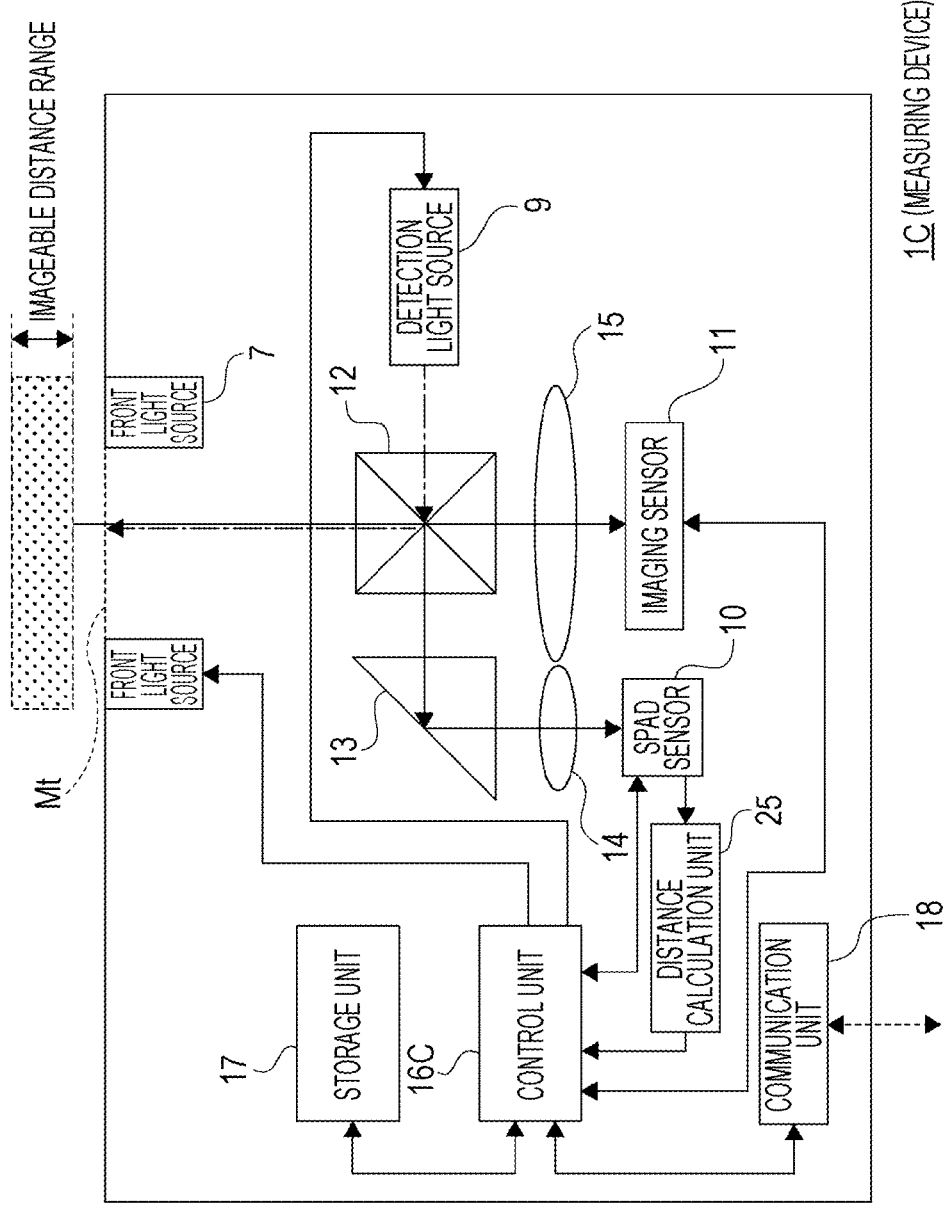
FIG. 29 is a block diagram illustrating an internal configuration example of a measuring device as a second modification.

FIG. 29 is a block diagram illustrating an internal configuration example of a measuring device 1C as a second modification that enables measurement of the target object without using the flow cell 5.

Differences from the measuring device 1 illustrated in FIG. 2 are that the flow cell 5 is omitted, the configuration related to intake and discharge of the sample with respect to the flow cell 5, specifically, the sample container 2, the cleaning liquid container 3 (including the sample intake port Mi), the sample switching unit 4, and the sample discharge unit 6 (including the sample discharge port Mo) are omitted, and the back light source 8 is omitted. Furthermore, the difference from the measuring device 1 is that a distance calculation unit 25 that calculates a distance to a light receiving reaction portion on the basis of a light reception signal of the SPAD sensor 10 is added, and a control unit 16C is provided instead of the control unit 16.

Here, the distance calculation unit 25 calculates the distance by, for example, a direct time of flight (ToF) method on the basis of the light reception signal of the SPAD sensor 10.

As illustrated in the drawing, in the measuring device 1C, light emitted from the detection light source 9 and reflected by the half mirror 12 is emitted to the sample as seawater existing outside the measuring device 1C via a light transmission window Mt. In the drawing, a range indicated as an "imageable distance range" schematically represents a distance range in which an image can be captured by the imaging sensor 11. The imageable distance range is defined as a focusable range in at least capturing an image by the imaging sensor 11 (range of depth of field).

Even in the case where the target object is detected on the basis of the light reception signal of the SPAD sensor 10, in a case where the position where the target object exists is a position outside the imageable distance range, an appropriate captured image of the target object by the imaging sensor 11 cannot be obtained, and appropriate measurement is difficult.

Therefore, in the second modification, the distance calculation unit 25 is provided to calculate the distance to the target object, and the imaging by the imaging sensor 11 is executed under a trigger condition that the target object is located in the imageable distance range.

Figure 30:
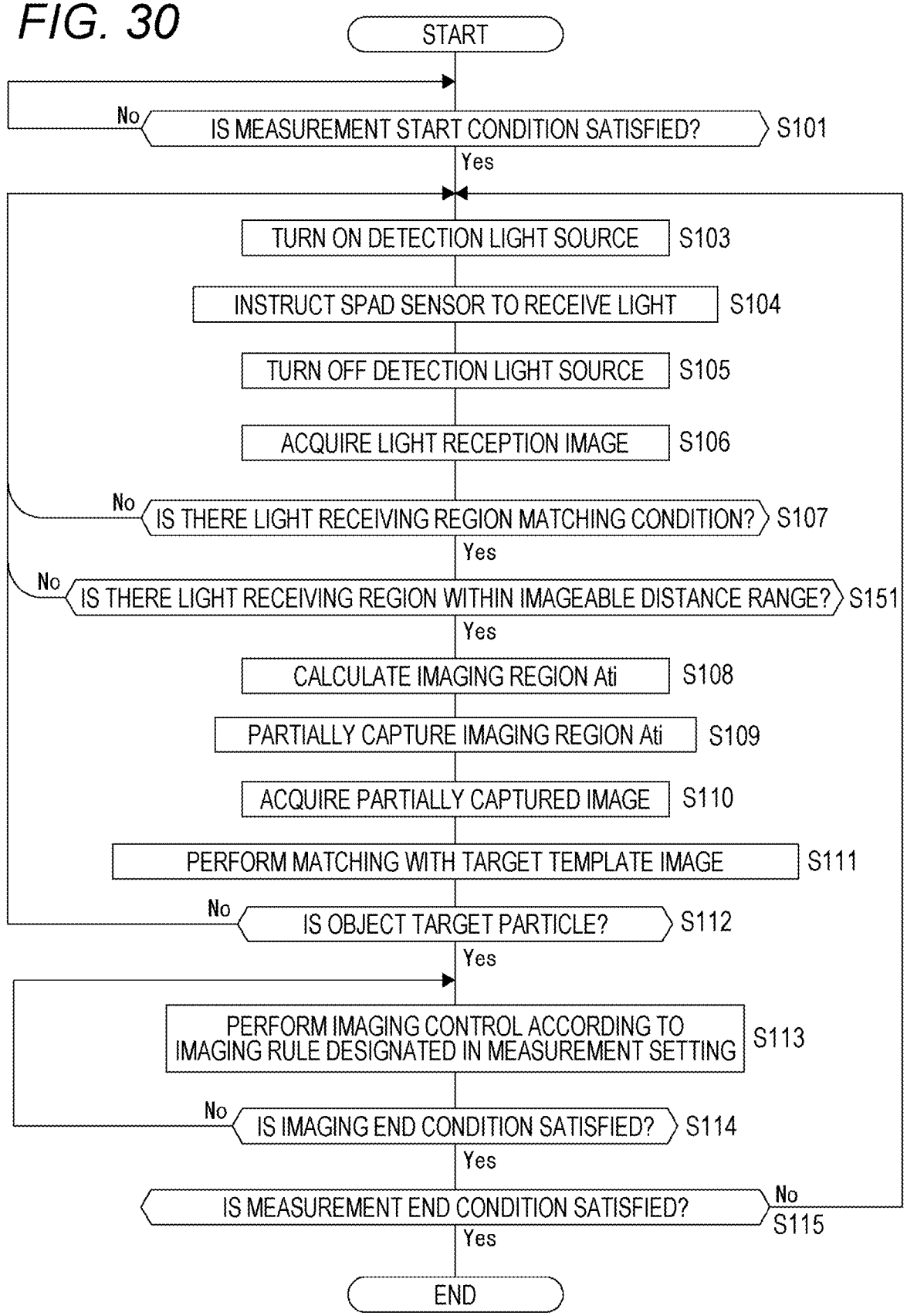
FIG. 30 is a flowchart illustrating a flow of processing from measurement start to measurement end in the second modification.

FIG. 30 is a flowchart illustrating a flow of processing from measurement start to measurement end in the second modification. Note that the processing in FIG. 30 is executed by the control unit 16C on the basis of a program stored in a predetermined storage device such as a built-in ROM, for example.

Differences from the processing illustrated in FIG. 17 are that the processing of starting sample injection in step S102 is omitted, determination processing in step S151 is inserted between steps S107 and S108, and the injection stop processing in step S116 and the cleaning processing in step S117 are omitted.

In step S151, the control unit 16C determines whether or not there is a light receiving region within the imageable distance range. That is, it is determined whether or not there is a light receiving region within the imageable distance range in the light receiving region Ats specified in step S107. Specifically, the control unit 16C acquires information of the distance to the light receiving region Ats specified in step S107 on the basis of distance information (depth image) obtained by the distance calculation unit 25, and determines, for all the specified light receiving regions Ats, whether or not the distance is a value within a distance range defined as the imageable distance range. If there is even one light receiving region Ats having the distance within the imageable distance range, the control unit 16C obtains a determination result that there is a light receiving region within the imageable distance range, and otherwise, obtains a determination result that there is no light receiving region within the imageable distance range.

In the case where it is determined that there is no light receiving region within the imageable distance range, the control unit 16C returns to step S103. That is, in the case where there is no light receiving region Ats within the imageable distance range, imaging by the imaging sensor 11 is not performed.

On the other hand, in the case where it is determined that there is a light receiving region within the imageable distance range, the control unit 16C advances the processing to step S108. Thereby, imaging by the imaging sensor 11 is performed on condition that there is the light receiving region Ats within the imageable distance range, and appropriate measurement can be performed in the configuration in which the flow cell 5 is omitted.

Note that, in the second modification, it goes without saying that the processing in and after step S108 is performed for the light receiving region Ats within the imageable distance range.

6-3. Third Modification

A third modification uses slit light as target object detection light in the case of adopting the configuration in which the flow cell 5 is omitted as in the second modification.

Figure 31:
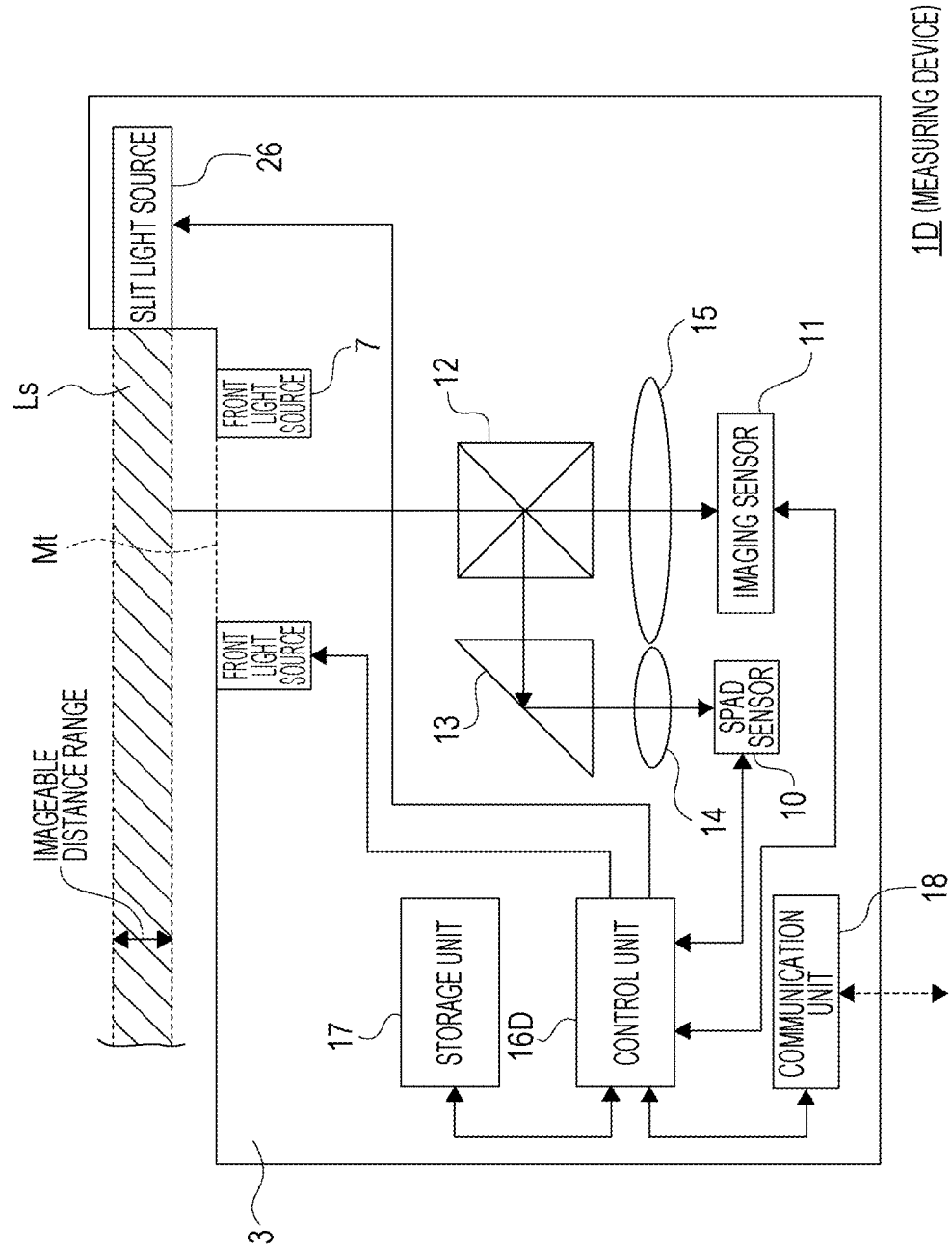
FIG. 31 is a block diagram illustrating an internal configuration example of a measuring device as a third modification.

FIG. 31 is a block diagram illustrating an internal configuration example of a measuring device 1D as a third modification.

Differences from the measuring device 1C illustrated in FIG. 29 are that a slit light source 26 is provided instead of the detection light source 9 and the distance calculation unit 25 is omitted.

As illustrated in the drawing, the slit light source 26 emits slit light Ls for illuminating the imageable distance range. Note that it is conceivable to use, for example, a semiconductor laser, a light emitting diode (LED), or the like for the slit light source 26.

By using the slit light Ls as described above, the reflected light is detected only from the target object located within the imageable distance range. Therefore, it is not necessary to obtain the distance to the target object in order to determine whether or not the target object is located within the imageable distance range as in the second modification, and the distance calculation unit 25 can be omitted.

A control unit 16D is different from the control unit 16C in the second modification in that the control processing (steps S103 and S105) of the detection light source is performed not for the detection light source 9 but for the slit light source 26, and the determination processing in step S151, that is, the determination processing as to whether or not there is the light receiving region within the imageable distance range is not executed, in the series of processing illustrated in FIG. 30

6-4. Fourth Modification

In a fourth modification, a digital holographic microscope is applied to an imaging system by the imaging sensor 11.

Figure 32:
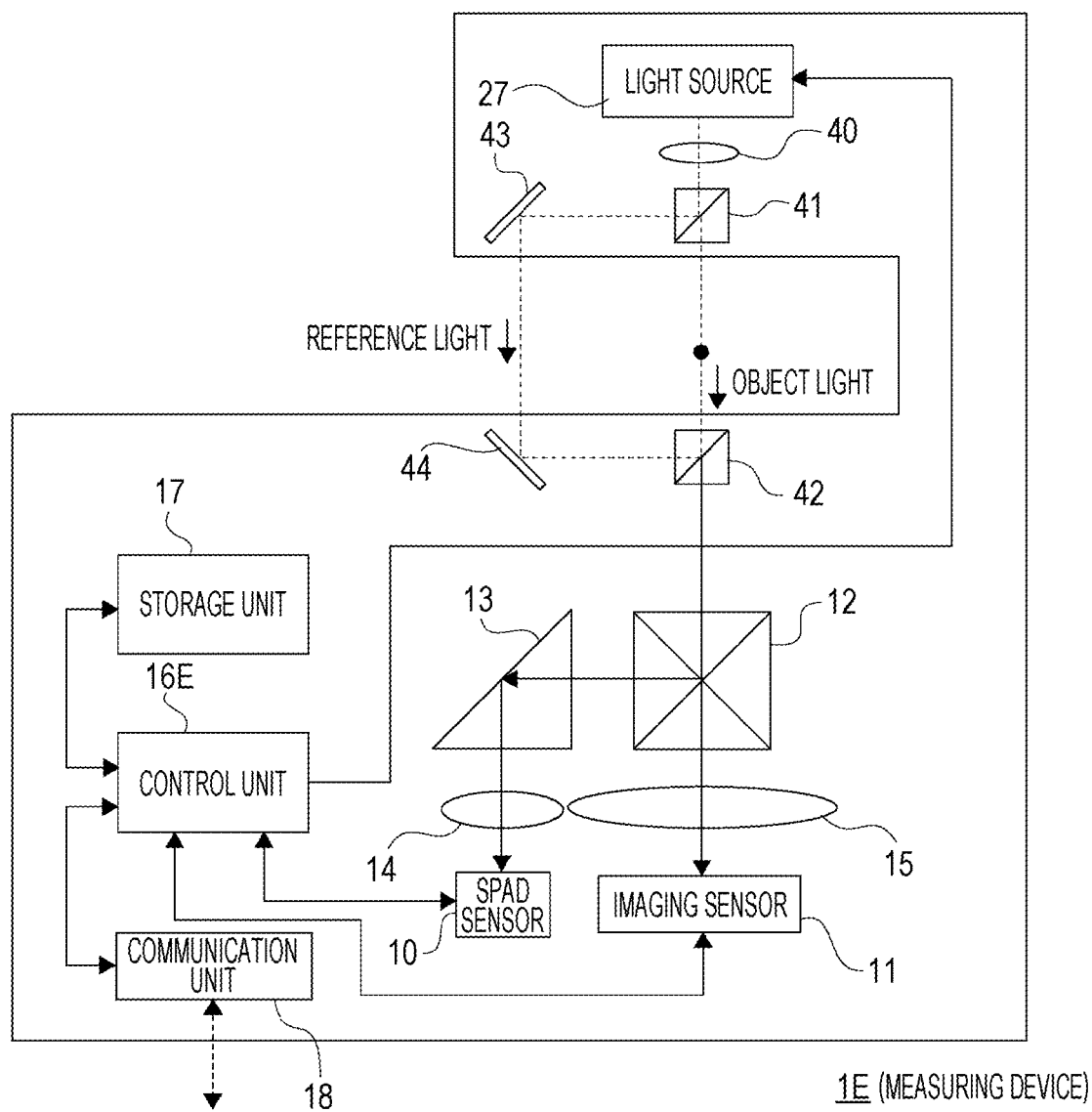
FIG. 32 is a block diagram illustrating an internal configuration example of a measuring device as a fourth modification.

FIG. 32 is a block diagram illustrating an internal configuration example of a measuring device 1E as the fourth modification.

As compared with the measuring device 1 illustrated in FIG. 2 described above, in the measuring device 1E, the flow cell 5, the configuration regarding the intake and discharge of the sample with respect to the flow cell 5 (sample container 2, cleaning liquid container 3, sample switching unit 4, and sample discharge unit 6), the front light source 7, the back light source 8, and the detection light source 9 are omitted. Furthermore, a control unit 16E is provided instead of the control unit 16.

In the measuring device 1E, a light source 27, a collimation lens 40, a beam splitter 41, a beam combining element 42, a mirror 43, and a mirror 44 are provided as an optical system for implementing the digital holographic microscope.

For example, a semiconductor laser is used as the light source 27, a part of coherent light emitted from the light source 27 is transmitted through the beam splitter 41 via the collimation lens 40 and is incident on the beam combining element 42 as object light, and the other part is reflected by the beam splitter 41 and is then incident on the beam combining element 42 via the mirrors 43 and 44 as illustrated in the drawing as reference light.

The beam combining element 42 transmits the incident object light and combines the reference light incident via the mirror 44 with the object light on the same optical axis to emit combined light to the half mirror 12.

As illustrated in the drawing, a part of the combined light incident on the half mirror 12 is transmitted and guided to the imaging sensor 11 side, and the other part is reflected and guided to the SPAD sensor 10 side.

The digital holographic technique is a technique in which a pattern of interference fringes between the object light and the reference light is imaged by an image sensor (imaging sensor 11), and a diffraction phenomenon of light is calculated from the imaged interference fringe pattern to obtain three-dimensional information of the object.

In a general microscope, the depth of field is relatively shallow, and for example, the depth of field of an objective lens for imaging fine particles such as plankton is about 1 mm. Therefore, when seawater is directly imaged in the vertical direction while diving, it is necessary to perform imaging a very large number of times while changing the depth.

Meanwhile, the digital holographic microscope can implement a depth of field that is about 100 times deeper than a lens imaging method using an objective lens. Therefore, when imaging is performed while moving a certain volume, the number of times of imaging can be greatly reduced as compared with a general microscope.

In the example illustrated in FIG. 32, the light emitted from the light source 27 is used to detect the target object using the SPAD sensor 10. In this case, the control unit 16E performs control to turn on the light source 27 and execute the imaging operation by the imaging sensor 11 in response to determination that there is a light receiving region Ats satisfying the condition on the basis of the light reception signal of the SPAD sensor 10.

Note that, as the light for target object detection using the SPAD sensor 10, light from a light source provided separately from the light source 27 can be used instead of the light emitted from the light source 27.

6-5. Fifth Modification

A fifth modification is a modification related to target object measurement based on the captured image by the imaging sensor 11.

In FIG. 18, the description has been given regarding recognizing the object region on the basis of the partially captured image of the imaging region Ati (S201), calculating the bounding box 20 on the basis of the recognized target object region (S202: see FIG. 16), calculating the ROI 21 on the basis of the calculated bounding box 20 (S203), performing the partial imaging for the ROI 21 in the next frame (S205), and performing the target object recognition processing in the ROI 21 (S206).

In such a series of processing, for the partial imaging for the ROI 21 performed in step S205, the image resolution can be made different according to the size of the ROI 21 calculated in step S203 (that is, the ROI 21 calculated in the previous frame).

A specific example will be described with reference to FIGS. 33 and 34.

Figure 33:
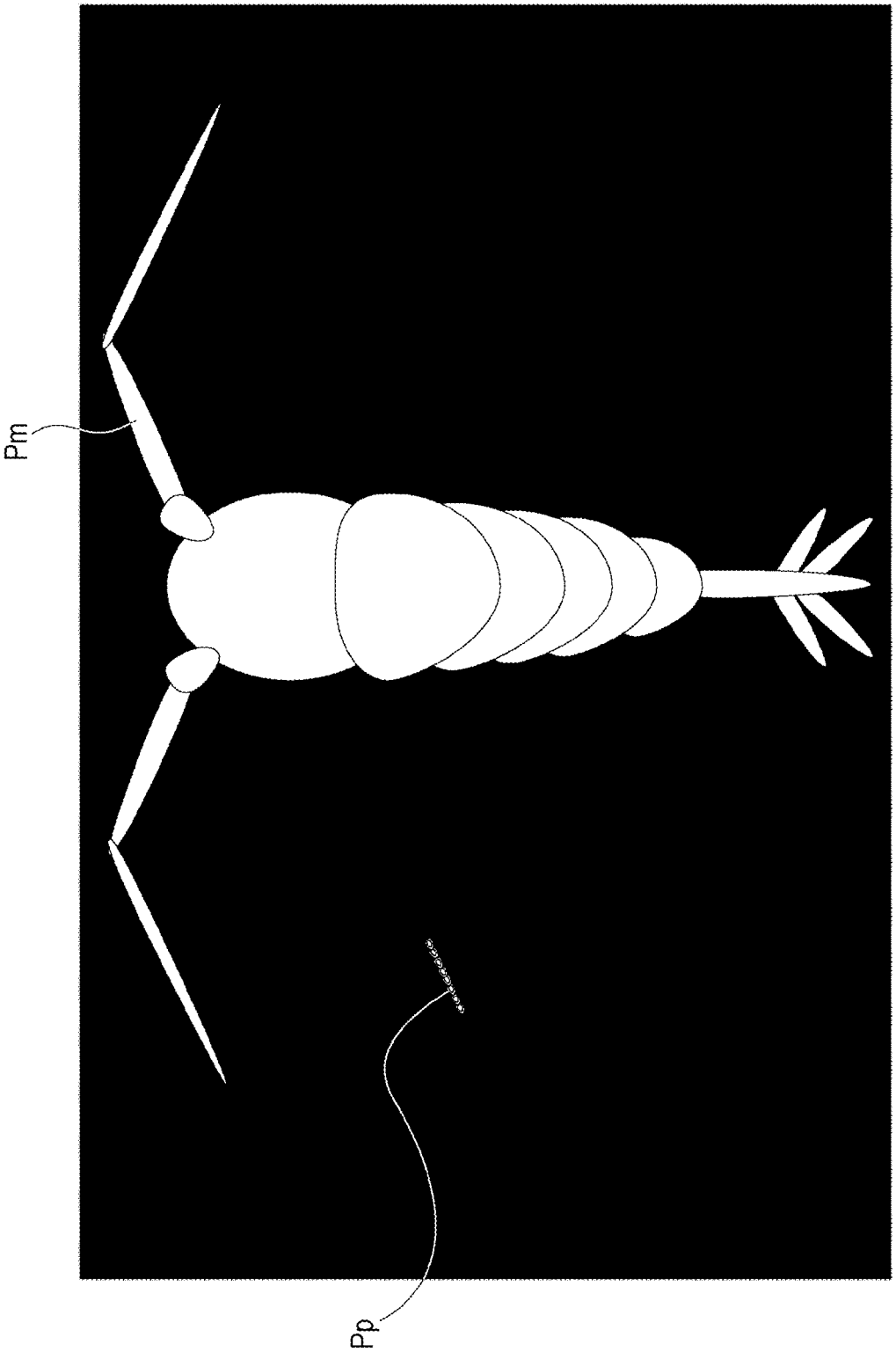
FIG. 33 is a view illustrating an example of a captured image in which zooplankton and phytoplankton are captured.
Figure 34:
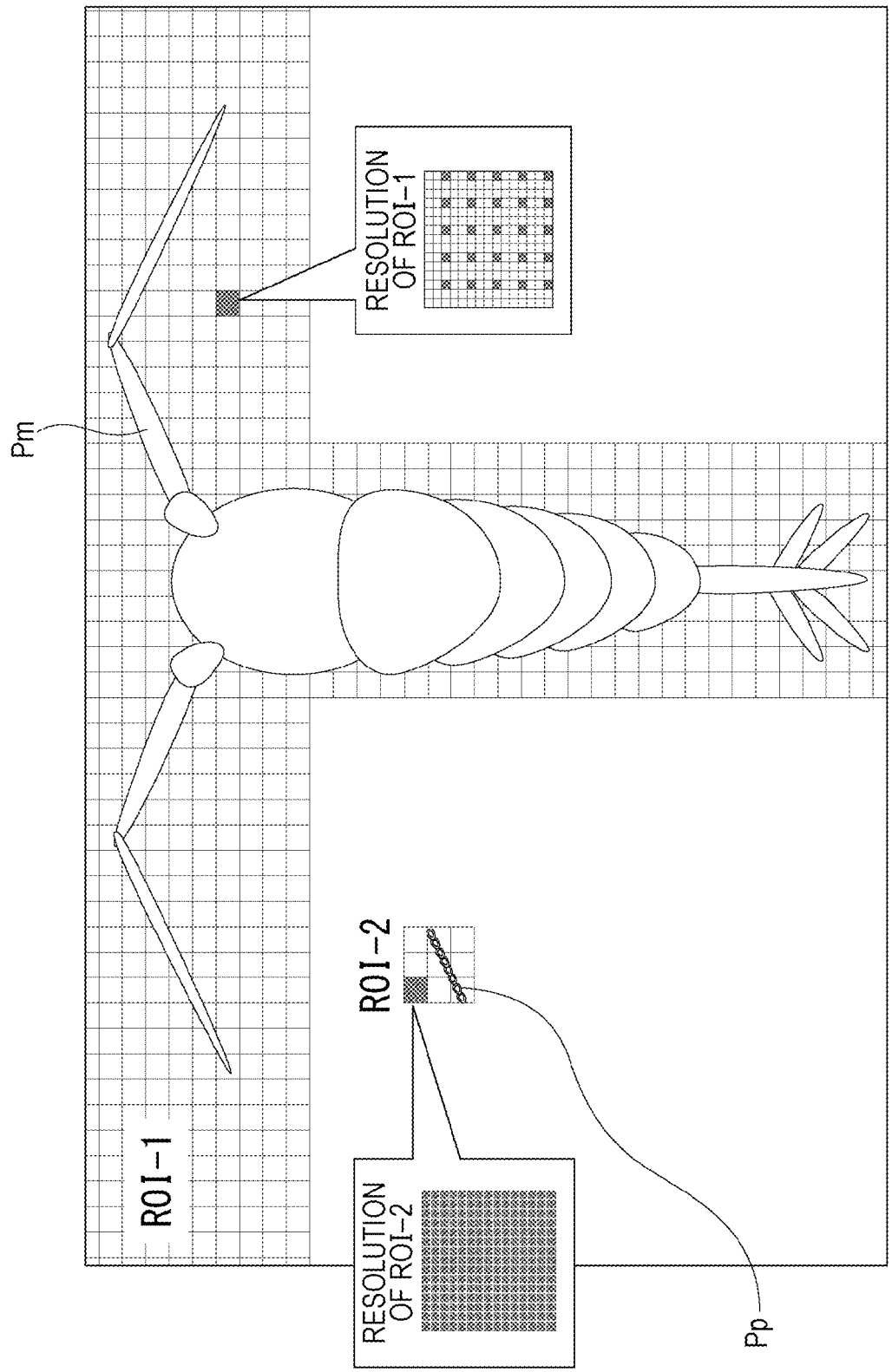
FIG. 34 is a view illustrating an ROI calculated for the zooplankton and an ROI calculated for the phytoplankton.

FIG. 33 illustrates an example in which zooplankton Pm and phytoplankton Pp are imaged as an example of the captured image by the imaging sensor 11, and FIG. 34 illustrates an ROI-1 that is an ROI 21 calculated for the zooplankton Pm and an ROI-2 that is an ROI 21 calculated for the phytoplankton Pp.

In general, the zooplankton Pm is larger than the phytoplankton Pp. For example, the zooplankton Pm such as *Calanus sinicus* has a length of about 2 mm to 3.5 mm, whereas the phytoplankton Pp such as *Skeletonema costatum* has a length about 0.06 mm.

In the fifth modification, in the case where the calculated size of the ROI 21 is small, control is performed to increase the image resolution in the partial imaging of the ROI 21 in the next frame as compared with the case where the calculated size is large. Specifically, in the example of FIG. 34, the image resolution of the ROI-2 of the phytoplankton Pp having a small size is set to the maximum (that is, no thinning), whereas the image resolution of the ROI-1 of the zooplankton Pm having a large size is set to the resolution obtained by thinning the image resolution to ⅑ (only one representative pixel is extracted from 3×3=9 pixels).

Here, in the target object recognition processing in step S206 (FIG. 18), it is possible to perform recognition for an object having a large size of the ROI 21 even if the image resolution is somewhat low, but there is a possibility that it becomes impossible to perform recognition for an object having a small size of the ROI 21 if the image resolution is lowered.

Therefore, in the present example, in the case where the calculated size of the ROI 21 is small, control is performed to increase the image resolution in the partial imaging of the ROI 21 in the next frame as compared with the case where the calculated size is large. Thereby, it is possible to prevent deterioration of the accuracy of the recognition processing for the object having the small size of the ROI 21 while reducing the recognition processing load for the object having the large size of the ROI 21. In other words, it is possible to achieve both the reduction of the recognition processing load and the prevention of the deterioration of the recognition processing accuracy.

Here, as can be seen with reference to FIGS. 33 and 34, according to the measurement method as the embodiment described so far, the target objects having different sizes can be simultaneously measured without changing the objective lens for each size of the target object.

6-6. Sixth Modification

In a sixth modification, detection of the target object, which has been performed using the SPAD sensor 10, is performed using the imaging sensor 11.

Figure 35:
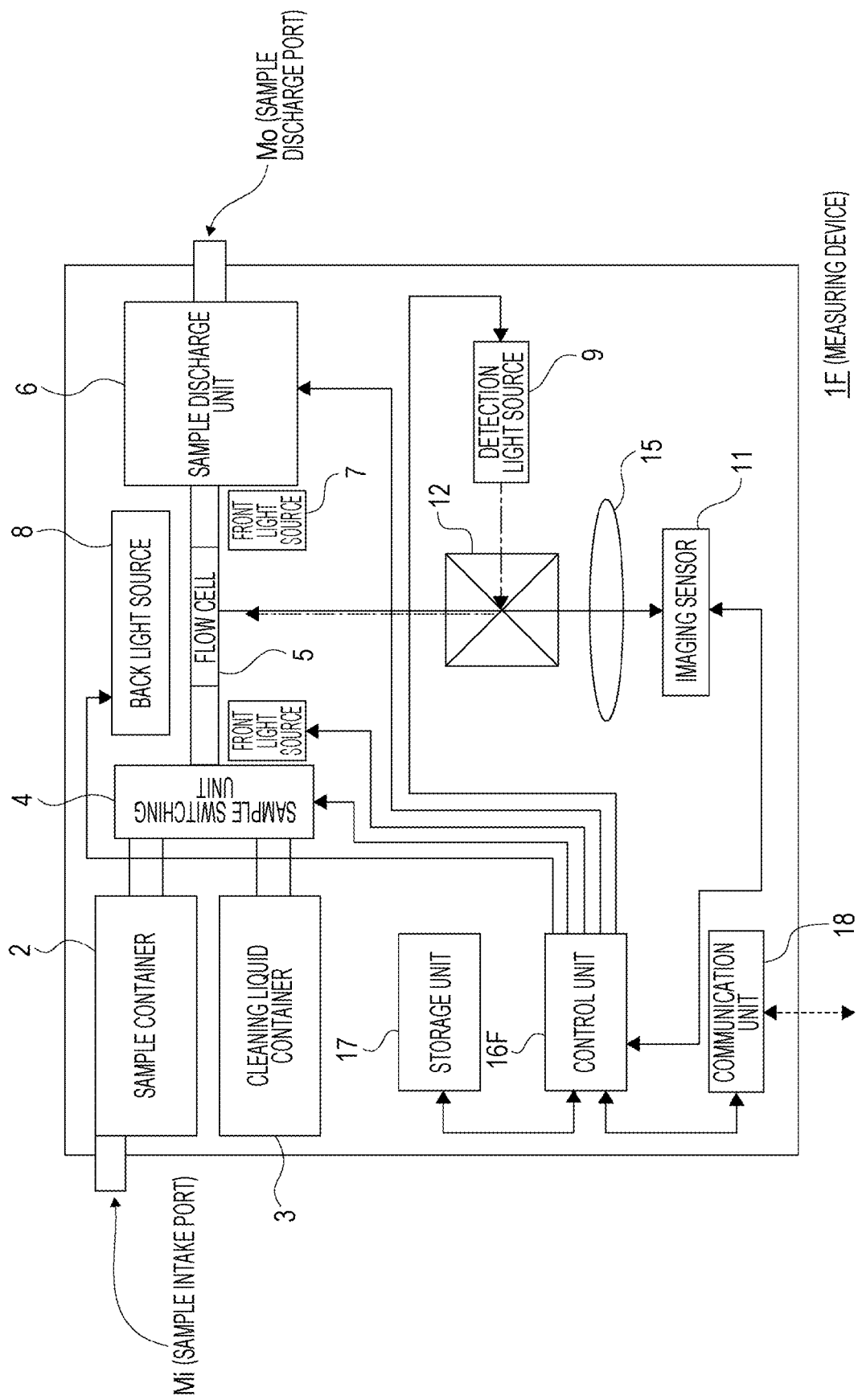
FIG. 35 is a block diagram illustrating an internal configuration example of a measuring device as a sixth modification.

FIG. 35 is a block diagram illustrating an internal configuration example of a measuring device 1F as the sixth modification.

Differences from the measuring device 1 illustrated in FIG. 2 is that the SPAD sensor 10, the mirror 13, and the lens 14 are omitted, and a control unit 16F is provided instead of the control unit 16.

In a case of enabling target object detection on the basis of weak return light from the target object such as excitation light due to a fluorescence reaction of phytoplankton, it is necessary to use the SPAD sensor 10 in order to enable detection of the weak return light.

However, in a case where return light having sufficiently higher light intensity than fluorescence reaction can be obtained, such as scattered light of zooplankton, the SPAD sensor 10 is unnecessary, and the return light can be detected by the imaging sensor 11 (image sensor). Therefore, in the sixth modification, the SPAD sensor 10 is omitted, and the target object detection processing is performed using the imaging sensor 11.

Figure 36:
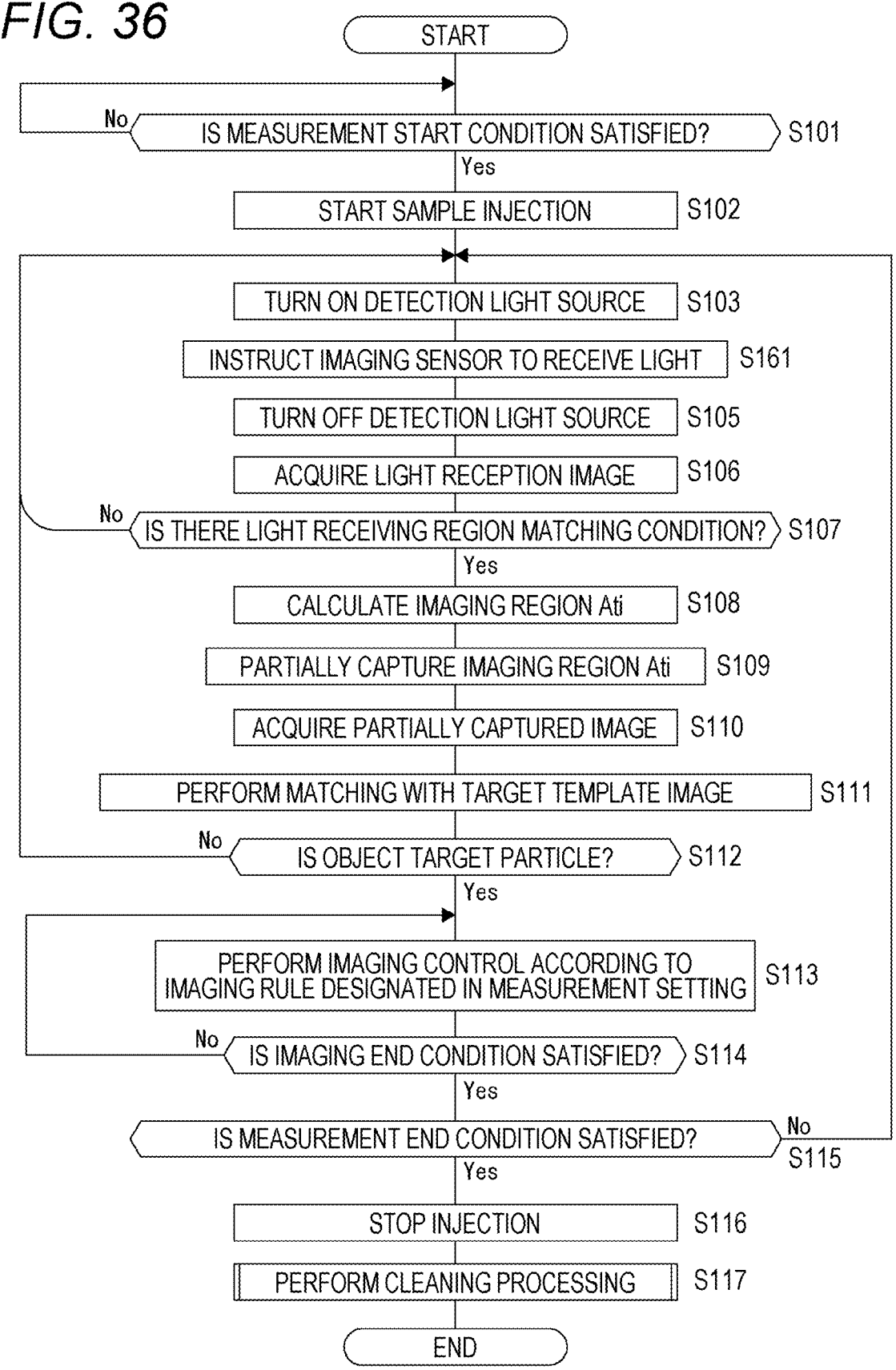
FIG. 36 is a flowchart illustrating a flow of processing from measurement start to measurement end in the sixth modification.

FIG. 36 is a flowchart illustrating a flow of processing from measurement start to measurement end in the sixth modification. The processing in FIG. 36 is executed by the control unit 16F on the basis of a program stored in a predetermined storage device such as a built-in ROM.

A difference from the processing illustrated in FIG. 17 is that light reception instruction processing in step S161 is performed instead of the light reception instruction processing in step S104.

Specifically, in step S161, the control unit 16F instructs the imaging sensor 11 to receive light. As a result, the determination processing in step S107, that is, the determination processing as to whether or not there is a light receiving region satisfying the condition is performed on the basis of the light reception image (captured image) by the imaging sensor 11.

Note that the imaging sensor 11 can adopt a configuration as a vision sensor that reads the light reception signal of a pixel at which an event occurs only when the event occurs. The vision sensor is a sensor called a dynamic vision sensor (DVS) or an event-based vision sensor (EVS), and is an asynchronous image sensor in which a plurality of pixels having photoelectric conversion elements is two-dimensionally arrayed, and a detection circuit that detects an address event in real time is provided for each pixel. The address event is an event that occurs for each address assigned to each of the plurality of two-dimensionally arrayed pixels. The event here is, for example, a current value based on a charge generated in the photoelectric conversion element, or a change amount of the charge exceeding a certain threshold value. The vision sensor detects the presence or absence of occurrence of an address event for each pixel, and reads a pixel signal from the pixel of the corresponding address as pixel data in the case where occurrence of the address event has been detected.

In the vision sensor as described above, since the pixel data is read from the pixel in which the occurrence of the address event is detected, it is possible to read the pixel at a much higher speed than a synchronous image sensor that reads all pixels at a predetermined frame rate, and the amount of data read as one frame is also small. Therefore, by using the vision sensor, the movement of the target object can be detected more quickly, and the frequency of the read operation can be reduced, so that the power consumption can be reduced.

Here, as can be seen with reference to FIG. 36, the control unit 16F in the sixth modification also performs matching between the captured image and the template image for a partial pixel range in which the target object is captured (see steps S108 to S111). At this time, as described in the modification in FIG. 26, the control unit 16F can perform class identification of an object captured in the captured image for the partial pixel range, and perform the matching using the template image of the identified class among the template images prepared for each class.

Furthermore, although not illustrated, the control unit 16F in the sixth modification also performs the processing for implementing tracking of the target object described in FIG. 18 and the like. Specifically, the calculation of the bounding box 20 and the calculation of the ROI 21 based on the bounding box 20 are performed, and the recognition processing for the target object in the ROI 21 and the like are performed.

Note that, in the above description, the application example to the type using the flow cell 5 has been described with respect to the sixth modification. However, it is also possible to adopt a configuration of a type in which the flow cell 5 is omitted as in the second and third modifications or a configuration of a type in which a digital holographic microscope is applied as in the fourth modification.

Here, in the above description, an example in which a plurality of pixels is two-dimensionally arrayed in the SPAD sensor (10 or 10B) has been described, but the SPAD sensor can also adopt a configuration in which a plurality of pixels is one-dimensionally arrayed. Alternatively, the SPAD sensor may be a single pixel sensor.

7. Summary of Embodiment

As described above, the first measuring device (measuring device 1, 1B, 16C, 16D, or 16E) of the embodiment includes the light emitting unit (detection light source 9 or 9B or slit light source 26) configured to emit light to a fluid, the light receiving unit (SPAD sensor 10 or 10B) configured to perform photoelectric conversion for incident light using an electron avalanche phenomenon by a plurality of pixels to obtain a light reception signal, and the control unit (16, 16B, 16C, 16D, or 16E) configured to perform processing of detecting a target object in the fluid on the basis of the light reception signal and execute an imaging operation of the target object on condition that the target object is detected.

According to the above configuration, it is possible to detect the presence or absence of the target object on the basis of the light reception signals of the plurality of pixels in reducing power consumption related to imaging by performing the imaging of the target object triggered by the detection of the target object on the basis of the light reception signal of the light receiving unit instead of constantly performing the imaging of the target object.

Therefore, it is possible to improve the detection accuracy of the presence or absence of the target object, and to achieve the power saving of the measuring device.

Since the power saving of the measuring device is achieved, it becomes possible to reduce the size of the battery as a power supply, and to reduce the size of the measuring device.

Furthermore, in the first measuring device as the embodiment, the light receiving unit includes the SPAD element as the photoelectric conversion element.

Thereby, it is not necessary to use a large-sized and high-power-consumption photoelectric conversion element such as a photomultiplier tube as the light receiving unit.

Therefore, it is possible to reduce the size and achieve the power saving of the light receiving unit, whereby it is possible to reduce the size and achieve the power saving of the measuring device.

Moreover, in the first measuring device as the embodiment, the control unit performs the target object detection processing on the basis of the image feature of the light receiving reaction portion in the light receiving unit (see S107 in FIGS. 17 and S301 in FIG. 28).

The "image feature of the light receiving reaction portion" referred to here means a feature of an image including at least one or more pixels having a light receiving reaction as the light receiving reaction portion, such as an image size or a position of the light receiving reaction portion, a wavelength of received light, or a value of the light reception signal.

It is possible to appropriately estimate whether or not the light receiving reaction portion captures the target object on the basis of the image feature of the light receiving reaction portion.

Moreover, in the first measuring device as the embodiment, the control unit prevents imaging of the imaging range corresponding to the light receiving reaction portion in the case where the image feature of the light receiving reaction portion does not match the designated image feature.

Thereby, it is possible to prevent an object other than an object having the designated image feature from being recklessly imaged.

Therefore, it is possible to reduce the power consumption related to imaging, and achieve the power saving of the measuring device.

Furthermore, in the first measuring device as the embodiment, the control unit detects the pixel position and the image size of the light receiving reaction portion as the image features (see FIGS. 12 to 14 and the like).

Thereby, it is possible to specify a pixel range in which the target object is captured, that is, a pixel range in which imaging is to be performed, for an imaging sensor that images the target object.

Thereby, it is possible to prevent an object other than an object having the designated image feature from being recklessly imaged, and to reduce the power consumption related to imaging.

Moreover, in the first measuring device as the embodiment, the control unit performs control such that, in the imaging sensor (imaging sensor 11 or 11B) that images the target object, the imaging operation is performed only for a partial pixel range in which the target object is captured.

Thereby, the power consumption related to imaging can be reduced as compared with a case where the imaging operation is performed for the entire pixel range in the imaging sensor.

Therefore, it is possible to achieve power saving of the measuring device.

Moreover, in the first measuring device as the embodiment, the control unit performs matching between the captured image and the template image for the partial pixel range (see S111 in FIG. 17).

By performing the matching based on the captured image, it is possible to appropriately identify the type of the target object.

Therefore, it is possible to improve the accuracy of the target object measurement by improving the recognition accuracy of the target object.

Furthermore, in the first measuring device as the embodiment, the control unit performs class identification of an object captured in the captured image for the partial pixel range, and performs the matching using the template image of the identified class among the template images prepared for each class.

By performing the image matching after narrowing the class in this manner, it is possible to improve the efficiency of the image matching processing.

Furthermore, in the first measuring device as the embodiment, the control unit sets a bounding box (bounding box 20) as a range surrounding the target object from the captured image of the partial pixel range and sets an ROI (ROI 21) that is a region including the bounding box and larger in size than the bounding box in a reference frame that is a predetermined frame when or after the target object is detected on the basis of the light reception signal, and sets the bounding box of the target object and sets the ROI based on the bounding box in the ROI set in a previous frame, in a frame after the reference frame (see FIG. 16).

Thereby, it is possible to track the target object even in a case where the target object moves in the captured image.

At this time, the captured image required in each frame for tracking the target object is only the captured image of the ROI. Therefore, in the case of tracking the target object to prevent erroneous counting, it is possible to narrow the imaging range for tracking only to the ROI, and it is possible to reduce the power consumption related to imaging for tracking.

Moreover, in the first measuring device as the embodiment, the sensor that functions as the light receiving unit and the imaging sensor that images the target object on the basis of control of the control unit are separated (see FIGS. 20 to 22).

Thereby, existing sensors can be used as a sensor that functions as the light receiving unit (a sensor that performs the photoelectric conversion using an electron avalanche phenomenon) and an imaging sensor that images a target object.

Therefore, it is not necessary to develop and use a new sensor, and it is possible to reduce the cost of the measuring device.

Furthermore, the first measuring device as the embodiment includes a single sensor having the function as the light receiving unit and the function to image the target object on the basis of control of the control unit (see FIGS. 24 and 25).

In the case of separately providing the sensors, it is necessary to provide a spectroscopic means for distributing light from the fluid to each of the sensors. However, the integrated sensor eliminates the need to provide such a spectroscopic means.

Therefore, it is possible to reduce the number of components of the optical component, and to reduce the size of the measuring device.

Furthermore, in the first measuring device as the embodiment, the flow cell (flow cell 5) in which the fluid is sampled with respect to the internal flow path is included, and the control unit causes a fluid different from the fluid as a sample to flow into the flow path to clean the flow cell after completion of the imaging operation (see FIG. 19).

Thereby, it is possible to prevent occurrence of erroneous measurement such as re-measurement of a measured target object.

Therefore, it is possible to improve the measurement accuracy of the target object.

Moreover, in the first measuring device as the embodiment, the control unit performs the target object detection processing on the basis of the light reception signal after the inflow of another fluid into the flow path (see S123 to S129 in FIG. 19).

Thereby, it is possible to confirm the presence or absence of a target object remaining after cleaning.

Therefore, it is possible to perform countermeasure processing for preventing erroneous measurement such as re-cleaning the flow cell in a case where there is a residual target object, and it is possible to enhance the effect of preventing the occurrence of erroneous measurement.

Furthermore, an imaging control method according to the embodiment is an imaging control method of a measuring device including at least a light emitting unit configured to emit light to a fluid and a light receiving unit configured to perform photoelectric conversion for incident light using an electron avalanche phenomenon by a plurality of pixels to obtain a light reception signal, the imaging control method including: performing processing of detecting a target object in the fluid on the basis of the light reception signal and executing an imaging operation of the target object on condition that the target object is detected.

According to such an imaging control method, it is also possible to obtain functions and effects similar to those of the first measuring device as the above-described embodiment.

A second measuring device (measuring device 1F) as the embodiment includes: a light emitting unit (detection light source 9, for example) configured to emit light to a fluid; an imaging sensor (imaging sensor 11) configured to perform photoelectric conversion for incident light by a plurality of pixels to obtain a light reception signal; and a control unit (control unit 16F) configured to perform processing of detecting a target object in the fluid on the basis of the light reception signal, and cause the imaging sensor to execute an imaging operation of the target object on condition that the target object is detected, in which the control unit performs control such that the imaging operation is performed only for a partial pixel range in which the target object is captured as the imaging operation of the target object.

According to the above configuration, it is possible to reduce the power consumption related to imaging by performing the imaging of the target object triggered by the detection of the target object on the basis of the light reception signal instead of constantly imaging the target object. Furthermore, the power consumption related to imaging can be reduced as compared with a case where the imaging operation is performed for the entire pixel range in the imaging sensor.

Therefore, it is possible to achieve power saving of the measuring device.

Furthermore, in the second measuring device as the embodiment, the control unit performs matching between the captured image and the template image for the partial pixel range.

By performing the matching based on the captured image, it is possible to appropriately identify the type of the target object.

Therefore, it is possible to improve the accuracy of the target object measurement by improving the recognition accuracy of the target object.

Moreover, in the second measuring device as the above-described embodiment, the control unit performs class identification of an object captured in the captured image for the partial pixel range, and performs the matching using the template image of the identified class among the template images prepared for each class.

By performing the image matching after narrowing the class in this manner, it is possible to improve the efficiency of the image matching processing.

Note that the effects described in the present specification are merely examples and are not limited, and other effects may be exhibited.

8. Present Technology

The present technology can also have the following configurations.

(1)
A measuring device including:
 a light emitting unit configured to emit light to a fluid;
 a light receiving unit configured to perform photoelectric conversion for incident light using an electron avalanche phenomenon to obtain a light reception signal; and
 a control unit configured to perform processing of detecting a target object in the fluid on the basis of the light reception signal and execute an imaging operation of the target object on condition that the target object is detected.

(2)
The measuring device according to (1), in which
 the light receiving unit includes a SPAD element as a photoelectric conversion element.

(3)
The measuring device according to (1) or (2), in which
 the control unit
 performs the processing of detecting the target object on the basis of an image feature of a light receiving reaction portion in the light receiving unit.

(4)
The measuring device according to (3), in which
 the control unit prevents imaging for an imaging range corresponding to the light receiving reaction portion in a case where the image feature of the light receiving reaction portion does not match a designated image feature.

(5)
The measuring device according to (3) or (4), in which
 the control unit
 detects, as the image feature, a pixel position and an image size of the light receiving reaction portion.

(6)
The measuring device according to any one of (1) to (5), in which
 the control unit
 performs control such that, in an imaging sensor that images the target object, the imaging operation is performed only for a partial pixel range in which the target object is captured.

(7)
The measuring device according to (6), in which
 the control unit
 performs matching between a captured image and a template image for the partial pixel range.

(8)
The measuring device according to (7), in which
 the control unit
 performs class identification of an object captured in the captured image for the partial pixel range, and performs the matching using the template image of an identified class among the template images prepared for each class.

(9)
The measuring device according to any one of (6) to (8), in which
 the control unit
 sets a bounding box as a range surrounding the target object from the captured image of the partial pixel range and sets an ROI that is a region including the bounding box and larger in size than the bounding box in a reference frame that is a predetermined frame when or after the target object is detected on the basis of the light reception signal, and
 sets the bounding box of the target object and sets the ROI based on the bounding box in the ROI set in a previous frame, in a frame after the reference frame.

(10)
The measuring device according to any one of (1) to (9), in which
 a sensor that functions as the light receiving unit and an imaging sensor that images the target object on the basis of control of the control unit are separated.

(11)
The measuring device according to any one of (1) to (9), further including:
 a single sensor having a function as the light receiving unit and a function to image the target object on the basis of control of the control unit.

(12)
The measuring device according to any one of (1) to (11), further including:
 a flow cell in which the fluid is sampled with respect to an internal flow path, in which
 the control unit
 causes a fluid different from the fluid as a sample to flow into the flow path to clean the flow cell after completion of the imaging operation.

(13)
The measuring device according to (12), in which
 the control unit performs the processing of detecting the target object on the basis of the light reception signal after the different fluid flows into the flow path.

(14)

An imaging control method of a measuring device including at least a light emitting unit configured to emit light to a fluid and a light receiving unit configured to perform photoelectric conversion for incident light using an electron avalanche phenomenon by a plurality of pixels to obtain a light reception signal, the imaging control method including:
performing processing of detecting a target object in the fluid on the basis of the light reception signal and executing an imaging operation of the target object on condition that the target object is detected.

(15)

A measuring device including:
a light emitting unit configured to emit light to a fluid;
an imaging sensor configured to perform photoelectric conversion for incident light by a plurality of pixels to obtain a light reception signal; and
a control unit configured to perform processing of detecting a target object in the fluid on the basis of the light reception signal, and cause the imaging sensor to execute an imaging operation of the target object on condition that the target object is detected, in which
the control unit
performs control such that the imaging operation is performed only for a partial pixel range in which the target object is captured as the imaging operation of the target object.

(16)

The measuring device according to (15), in which
the control unit
performs matching between a captured image and a template image for the partial pixel range.

(17)

The measuring device according to (16), in which
the control unit
performs class identification of an object captured in the captured image for the partial pixel range, and performs the matching using the template image of an identified class among the template images prepared for each class.

REFERENCE SIGNS LIST 1, 1B, 1C, 1D, 1E, 1F Measuring device
2 Sample container
3 Cleaning liquid container
4 Sample switching unit
5 Flow cell
6 Sample discharge unit
7 Front light source
8 Back light source
9, 9B Detection light source
10, 10B SPAD sensor
11, 11A, 10B Imaging sensor
12 Half mirror
13 Mirror
14, 15 Lens
16, 16B, 16C, 16D, 16E, 16F Control unit
17 Storage unit
18 Communication unit
Mi Sample intake port
Mo Sample discharge port
20 Bounding box
21 ROI
G10, G11, and Gmx Pixel
30 Bus
31 Pixel array unit
32 ADC/pixel selector
33 Buffer
34 Logic unit
35 Memory
36 Interface unit
37 Calculation unit
37a Image processing unit

The invention claimed is:

1. A measuring device comprising:
a light source configured to emit light to a fluid;
a first sensor configured to perform photoelectric conversion for incident light using an electron avalanche phenomenon by a plurality of pixels to obtain a light reception signal; and
a processing circuitry configured to:
receive the light reception signal of the first sensor, the light reception signal indicating that one or more of the pixels of the first sensor has a light receiving reaction,
determine whether a feature of the one or more of the pixels of the first sensor that has the light receiving reaction matches a designated feature,
execute an imaging operation of a target object in the fluid by a second sensor having a lower light receiving resolution than the first sensor on a condition that the feature of the one or more of the pixels of the first sensor that has the light receiving reaction matches the designated feature, and
avoid the imaging operation by the second sensor in a case where the feature of the one or more of the pixels of the first sensor that has the light receiving reaction does not match the designated feature.

2. The measuring device according to claim 1, wherein first sensor includes a Single-Photon Avalanche Diode (SPAD) element as a photoelectric conversion element.

3. The measuring device according to claim 1, wherein the feature of the one or more of the pixels of the first sensor that has the light receiving reaction includes an image feature of an image including the one or more of the pixels of the first sensor that has the light receiving reaction.

4. The measuring device according to claim 1, wherein the processing circuitry is configured to prevent the imaging operation for an imaging range corresponding to the one or more of the pixels of the first sensor that has the light receiving reaction in the case where the feature of the one or more of the pixels of the first sensor that has the light receiving reaction does not match the designated feature.

5. The measuring device according to claim 3, wherein the image feature includes a pixel position and an image size of the image including the one or more of the pixels of the first sensor that has the light receiving reaction.

6. The measuring device according to claim 1, wherein the processing circuitry is configured to perform control such that, in the second sensor, the imaging operation is performed only for a partial pixel range.

7. The measuring device according to claim 6, wherein the processing circuitry is configured to perform matching between a captured image and a template image for the partial pixel range.

8. The measuring device according to claim 7, wherein the processing circuitry is configured to:
perform class identification of an object captured in the captured image for the partial pixel range, and perform the matching using the template image of an identified class among template images prepared for each class.

9. The measuring device according to claim 6, wherein the processing circuitry is configured to:
set a bounding box as a range surrounding the target object from the partial pixel range and set an ROI that is a region including the bounding box and is larger in size than the bounding box in a reference frame that is a predetermined frame when or after the feature of the one or more of the pixels of the first sensor that has the light receiving reaction matches the designated feature, and
set the bounding box of the target object and set the ROI based on the bounding box in the ROI set in a previous frame, in a frame after the reference frame.

10. The measuring device according to claim 1, wherein the first sensor and the second sensor are separated.

11. The measuring device according to claim 1, wherein the first sensor is a single sensor having a function of the first sensor and a function of the second sensor.

12. The measuring device according to claim 1, further comprising:
a flow cell in which the fluid is sampled with respect to an internal flow path,
wherein the processing circuitry is configured to cause a fluid different from the fluid as a sample to flow into the flow path to clean the flow cell after completion of the imaging operation.

13. The measuring device according to claim 12, wherein the processing circuitry is configured to perform the determining whether the feature of the one or more of the pixels that has the light receiving reaction matches the designated feature after the different fluid flows into the flow path.

14. The measuring device according to claim 1, wherein the designated feature includes that the one or more of the pixels include more than one pixels that have the light receiving reaction and the more than one pixels that have the light receiving reaction are adjacent to one another.

15. The measuring device according to claim 1, wherein the designated feature includes a designed size of the one or more of the pixels of the first sensor that has the light receiving reaction.

16. The measuring device according to claim 15, wherein the designated feature includes a designed wavelength of the one or more of the pixels of the first sensor that has the light receiving reaction.

17. An imaging control method comprising:
receiving a light reception signal of a first sensor configured to perform photoelectric conversion for incident light using an electron avalanche phenomenon by a plurality of pixels to obtain the light reception signal, the light reception signal indicating that one or more of the pixels of the first sensor has a light receiving reaction,
determining whether a feature of the one or more of the pixels of the first sensor that has the light receiving reaction matches a designated feature,
executing an imaging operation of a target object in a fluid by a second sensor having a lower light receiving resolution than the first sensor on a condition that the feature of the one or more of the pixels of the first sensor that has the light receiving reaction matches the designated feature, and
avoiding the imaging operation by the second sensor in a case where the feature of the one or more of the pixels of the first sensor that has the light receiving reaction does not match the designated feature.

18. A measuring device comprising:
a light source configured to emit light to a fluid;
a first sensor configured to perform photoelectric conversion for incident light by a plurality of pixels to obtain a light reception signal; and
processing circuitry configured to:
receive the light reception signal of the first sensor, the light reception signal indicating that one or more of the pixels of the first sensor has a light receiving reaction,
determine whether a feature of the one or more of the pixels of the first sensor that has the light receiving reaction matches a designated feature,
cause the first sensor to execute an imaging operation of a target object in the fluid by a second sensor having a lower light receiving resolution than the first sensor on a condition that the feature of the one or more of the pixels of the first sensor that has the light receiving reaction matches the designated feature, the imaging operation being only for a partial pixel range of the second sensor, and
avoid the imaging operation by the second sensor in a case where the feature of the one or more of the pixels of the first sensor that has the light receiving reaction does not match the designated feature.

19. The measuring device according to claim 18, wherein the processing circuitry is configured to perform matching between a captured image and a template image for the partial pixel range.

20. The measuring device according to claim 19, wherein the processing circuitry is configured to:
perform class identification of an object captured in the captured image for the partial pixel range, and
perform the matching using the template image of an identified class among template images prepared for each class.

* * * * *